(12) United States Patent
Hud

(10) Patent No.: US 7,368,560 B2
(45) Date of Patent: May 6, 2008

(54) INTERCALATION-MEDIATED SYNTHESIS OF POLYMERS

(75) Inventor: Nicholas V. Hud, Decatur, GA (US)

(73) Assignee: Georgia Tech Research Corp., Atlanta, GA (US)

( * ) Notice: Subject to any disclaimer, the term of this patent is extended or adjusted under 35 U.S.C. 154(b) by 195 days.

(21) Appl. No.: 10/948,712

(22) Filed: Sep. 23, 2004

(65) Prior Publication Data

US 2005/0202459 A1    Sep. 15, 2005

Related U.S. Application Data

(60) Provisional application No. 60/505,365, filed on Sep. 23, 2003.

(51) Int. Cl.
*C07H 21/00* (2006.01)
*C12Q 1/68* (2006.01)

(52) U.S. Cl. .................. 536/25.3; 536/23.1; 435/6; 435/91.2

(58) Field of Classification Search ............. None
See application file for complete search history.

(56) References Cited

U.S. PATENT DOCUMENTS 4,828,979 A * 5/1989 Klevan et al. ............ 435/6
5,864,026 A * 1/1999 Jensen et al. ........... 536/23.1
5,994,056 A * 11/1999 Higuchi .................... 435/6

OTHER PUBLICATIONS

Kubar et al. Binding of Cationic and Neutral Phenanthridine Intercalators to a DNA Oligomer Is Controlled by Dispersion Energy: Quantum Chemical Calculations and Molecular Mechanics Simulations. Chemistry-A European Journal, (2006) vol. 12, No. 1, pp. 280-290.*
Jain et al. Enzymatic Behavior by Intercalating Molecules in a Template-Directed Ligation Reaction. Angewandte Chemie International Edition, (2004) vol. 43, No. 15, pp. 2004-2008.*
Montecucco et al. Effects of DNA-binding drugs on T4 DNA ligase. Biochem J. Mar. 1, 1990; 266(2): 379-384.*
Jain, S. Nucleic acid assembly using small molecule interactions: A thesis presented to the academic faculty. (Aug. 2006).*
Armitage et al. Peptide nucleic acid (PNA)/DNA hybrid duplexes: intercalation by an internally linked anthraquinone. Nucleic Acids Research, 1998, vol. 26, No. 3, pp. 715-720.*
Lewin, B. Genes V. Oxford University Press (1994), pp. 266-267.*
Beaucage SL, Bergstrom DE, et al. In: Current Protocols in Nucleic Acid Chemistry; 2000; Appendix 6.1.8-9, Appendix 3B, Appendix 3C.

(Continued)

*Primary Examiner*—Young J. Kim
*Assistant Examiner*—Samuel Woolwine
(74) *Attorney, Agent, or Firm*—Thomas, Kayden, Horstemeyer & Risley LLP; Todd Deveau

(57) ABSTRACT

Methods and compositions for synthesizing biopolymers using an intercalator are provided. Aspects provide compositions and methods for synthesizing biopolymers with non-natural backbones or non-natural biopolymer subunits using natural biopolymer templates. Other aspects provide compositions and methods for synthesizing biopolymers using a template with a non-natural backbone on non-natural biopolymer subunits.

47 Claims, 13 Drawing Sheets

OTHER PUBLICATIONS

Dolinnaya, NG, et al. Site-directed modification of DNA duplexes by chemical ligation. In: Nucleic Acids Research; 1988; 3721-3738.

Grunenwald, H. Optimizzation of Polymerase Chain Reactions. In: Methods in Molecular Biology; 2003; 226:89-99.

Gryaznov SM, Schultz R, et al. Enhancement of selectivity in recognition of nucleic-acids via chemical autoligation. In: Nucleic Acids Research; 1994; 22:2366-2369.

Kanavarioti A, Bernasconi CF and Barid ED. Effects of monomer and template concentration on the kinetics of nonezymatic template-directed oligoguanylate synthesis. In: Journal of the American Chemical Society; 1998; 120:8575-8581.

Kanaya E and Yanagawa H. Template-directed polymerization of oligoadenylates using cyanogen-bromide. In: Biochemistry; 1986; 25:7423-7430.

Pritchard CE and Southern EM. Effects of base mismatches on joining of short oligodeoxynucleotides by DNA ligases. In: Nucleic Acids Research; 1997; 25:3403-3407.

Rohatgi R, Bartel DP and Szostak JW. Kinetic and mechanistic analysis of nonenzymatic, template-directed oligoribonucleotide ligation. In: Journal of the American Chemical Society; 1996; 118:3332-3339.

Shabarova ZA, Dolinnaya NG, et al. DNA-like duplexes with repetitions. III. Efficient template-guided chemical polymerization of d(TGGCCAAGCTp). In: Nucleic Acids Research; 1981; 9(21):5747-5761.

Shabarova ZA, Ivanovskaya MG and Isaguliants MG. DNA-like duplexes with repetitions-efficient template-guided polycondensation of decadeoxyribonucleotide imidazolide. In: FEBS Letters; 1983; 154:288-292.

Szostak JW. Introduction: Combinatorial chemistry. In: Chemical Reviews; 1997; 97:347-348.

von Kiedrowski G. A self-replicating hexadeoxynucleotide. In: Angewandte Chemie International Edition in English; 1986; 25:932-935.

Xu YZ and Kool ET. High sequence fidelity in a non-enzymatic DNA autoligation reaction. In: Nucleic Acids Research; 1999; 27:875-881.

Zuber G and Behr JF. Nonenzymatic plasmid ligation mediated by minor groove-binding molecules. In: Biochemistry; 1994; 33:8122-8127.

* cited by examiner

A    B

A

B

C

D

E

F 9-aminoacridine acridine orange proflavine ellipticine ethidium daunomycin

T·A·T base triplet

Coralyne

SEQUENCE LISTING

```
<160> NUMBER OF SEQ ID NOS: 9

<210> SEQ ID NO 1
<211> LENGTH: 4
<212> TYPE: DNA
<213> ORGANISM: Artificial Sequence
<220> FEATURE:
<223> OTHER INFORMATION: synthetic substrate strand

<400> SEQUENCE: 1 tcga                                                                    4

<210> SEQ ID NO 2
<211> LENGTH: 3
<212> TYPE: DNA
<213> ORGANISM: Artificial Sequence
<220> FEATURE:
<223> OTHER INFORMATION: synthetic substrate strand

<400> SEQUENCE: 2 ctc                                                                     3

<210> SEQ ID NO 3
<211> LENGTH: 4
<212> TYPE: DNA
<213> ORGANISM: Artificial sequence
<220> FEATURE:
<223> OTHER INFORMATION: synthetic substrate strand

<400> SEQUENCE: 3 cgta                                                                    4

<210> SEQ ID NO 4
<211> LENGTH: 11
<212> TYPE: DNA
<213> ORGANISM: Artificial sequence
<220> FEATURE:
<223> OTHER INFORMATION: synthetic template strand

<400> SEQUENCE: 4
agctgcatga g                                                           11
```

```
<210> SEQ ID NO 5
<211> LENGTH: 11
<212> TYPE: DNA
<213> ORGANISM: Artificial sequence
<220> FEATURE:
<223> OTHER INFORMATION: product strand, combined SEQ ID Nos. 1, 2,
      and 3

<400> SEQUENCE: 5
tcgacgtact c                                                        11

<210> SEQ ID NO 6
<211> LENGTH: 3
<212> TYPE: DNA
<213> ORGANISM: Artificial sequence
<220> FEATURE:
<223> OTHER INFORMATION: synthetic substrate strand

<400> SEQUENCE: 6 ttt                                                                 3

<210> SEQ ID NO 7
<211> LENGTH: 4
<212> TYPE: DNA
<213> ORGANISM: Artificial sequence
<220> FEATURE:
<223> OTHER INFORMATION: synthetic substrate strand

<400> SEQUENCE: 7 tttt                                                                4

<210> SEQ ID NO 8
<211> LENGTH: 23
<212> TYPE: DNA
<213> ORGANISM: Artificial sequence
<220> FEATURE:
<223> OTHER INFORMATION: synthetic template hairpin

<400> SEQUENCE: 8
gcaaaaaaag gaactttttt tgc                                           23

<210> SEQ ID NO 9
<211> LENGTH: 7
<212> TYPE: DNA
<213> ORGANISM: Artificial sequence
<220> FEATURE:
<223> OTHER INFORMATION: product strand, combined Seq ID Nos 6 and 7

<400> SEQUENCE: 9 ttttttt                                                             7
```

INTERCALATION-MEDIATED SYNTHESIS OF POLYMERS

CROSS-REFERENCE TO RELATED APPLICATION

This application claims priority to and benefit of U.S. provisional patent application No. 60/505,365 filed on Sep. 23, 2003, which is incorporated by reference in its entirety.

BACKGROUND

1. Technical Field

The present disclosure generally relates to methods and compositions for the synthesis of biopolymers, in particular natural or non-natural nucleic acids and analogous polymers.

2. Related Art

DNA and RNA oligonucleotides, and their structural analogs, have found numerous applications as diagnostic and therapeutic agents. Nucleic acids are the polymers used by living organisms for the storage of genetic information, and are thus a primary therapeutic target for the treatment of genetic and acquired diseases, and for vaccine development. During the past decade, interest in anti-sense and anti-gene therapy has motivated the development of DNA and RNA molecules that bind at specific points within the human genome or to specific messenger RNA sequences. More recently, the discovery of small RNA molecules that naturally interfere with gene expression has presented additional possibilities for how RNA may also be used to treat acquired and genetic diseases. Thus, methods to prepare RNA, DNA, and polymers in large scale are of great importance to the medical field for drug development and will soon be for use as therapeutics.

Living organisms, including humans, have developed protective mechanisms to degrade foreign nucleic acids that gain entry to the cells or the intercellular fluid of the organism. Such foreign, or exogenous, nucleic acids include RNA and DNA polymers introduced by naturally-occurring viruses. These same anti-pathogen defense mechanisms, however, also limit the lifetime of nucleic acid polymers introduced into a human body for therapeutic purposes. Thus, it is of great importance to develop methods for the improved synthesis of non-natural structural analogs of RNA and DNA that can function in similar capacities as natural nucleic acid polymers, but that are not susceptible to the same modes of enzymatic degradation. Structural analogs of the natural nucleic acids (or "non-natural" nucleic acids) include, but are not limited to, DNA and RNA-like polymers in which the natural backbone has been modified by the addition or removal of one or more chemical groups. These modifications range from the methylation of the ribose sugar, to the radical replacement of the backbone with a peptide-like backbone. Broadly defined, nucleic acids analogs, or non-natural nucleic acids, are any polymers that have chemical appendages to the polymer backbone similar in chemical structure to the natural nucleotide bases (i.e. A, adenine; C, cytosine; G, guanine; U, uridine; T, thymine) that allow the formation of base pairs for the transfer of nucleotide sequence information. Although the synthesis of natural nucleic acid polymers has become routine in many commercial and academic laboratories, the synthesis of non-natural nucleic acid polymers (i.e., synthetic analogs) is typically much more expensive and can require a substantial investment of time and resources for the development of a synthetic procedure for each new variation in nucleic acid chemical structure. Thus, methods that can facilitate the synthesis of natural and non-natural nucleic acids are of great economic and medicinal importance.

RNA and DNA molecules with a wide range of novel properties, including catalytic, molecular recognition and therapeutic activities, have been isolated from pools of RNA and DNA polymers, respectively, that initially contain a large number of random nucleotide sequences. This process is accomplished by multiple rounds of activity-based selection for nucleic acid molecules with a desired property from the pool of random sequences, followed by the enzymatic amplification of selected sequences using naturally-derived polymerases. Known as "in vitro selection" or "SELEX", this procedure represents one of the most powerful forms of combinatorial chemistry.

The enzymatic amplification of nucleic acid sequences during each cycle of the SELEX procedure is an essential component of this procedure, as nucleic acid amplification leads to the exponential enrichment of sequences in a sample that have the desired molecular properties. The polymerases used to amplify nucleic acid molecules as part of the SELEX process were initially isolated from living organisms, and are still produced within host cells by fermentation. The amino acid sequences of these polymerases are either identical to that derived from a natural source, or are a genetically-modified variant of a natural polymerase. Natural polymerases or derivatives thereof cannot synthesize non-natural nucleic acids.

A process similar to SELEX for the selective amplification of non-natural RNA-like polymers would undoubtedly produce molecules superior to RNA for many applications. For example, an RNA-like polymer with a backbone that is resistant to cleavage and degradation by natural ribonucleases could be far more effective as an antibiotic because it would have a longer active time within the body. Another example would be the selection of a catalytic RNA-like polymer with a non-natural backbone that has charged groups with a pKa near neutrality. Such a catalyst would be sensitive to pH, and thus small changes in pH could be used to regulate catalytic activity. However, because naturally-derived nucleic acid polymerases can only replicate RNA or DNA, the realization of in vitro selection with non-natural polymers will either require extensive evolution of existing polymerases, or the development of new methods for molecular replication. An editorial on the SELEX procedure by a pioneer of this technique clearly states that the ability to accomplish in vitro selection using naturally-derived polymerases comes with the severe limitation that selection can only be carried out with natural polymers (Szostak, 1997). Thus, it is well appreciated by experts in this field that methods to replicate non-natural polymers would greatly expand the power of in vitro selection. Accordingly, the development of improved methods for the enzyme-free synthesis of nucleic acids and analogous polymers could be of great value to the fields of polymer chemistry, materials science, biotechnology and medicine.

Those skilled in the art of nucleic acid synthesis have toiled for decades to improve methods for enzyme-free template-directed synthesis of nucleic acids with only modest gains. For example, considerable effort has focused on the potential for inorganic cations to improve existing methods for the chemical coupling of nucleic acids in aqueous solution (Lohrmann et al, 1980; Rohatgi et al., 1996). In contrast, virtually no studies have investigated the possibility that a specific interaction between a small molecule and the nucleic acid bases could be used to enhance enzyme-free synthesis of nucleic acid polymers.

Thus, the collective body of research conducted by the scientific and medical communities demonstrates a need for more efficient methods for the chemical ligation of both natural and non-natural oligonucleotides in aqueous solution. Furthermore, there is a need for methods to efficiently couple nucleic acid polymers in solution using catalysts that are easily separated from the product molecules, so that the products can subsequently be used in therapeutic applications. An efficient, enzyme-free method for the coupling of both natural and non-natural nucleic acid oligonucleotides along a template strand would have substantial commercial value, as such methods will enable the in vitro selection of non-natural nucleic acid polymers with desirable therapeutic and catalytic properties.

SUMMARY

Aspects of the present disclosure generally provide compositions and methods for the synthesis of polymers, for example biopolymers such as nucleic acids. One aspect provides compositions and methods for synthesizing non-natural biopolymers using a natural biopolymer template and at least one non-natural biopolymer subunit. Another aspect provides compositions and methods for synthesizing biopolymers using a non-natural biopolymer template and biopolymer subunits. Certain aspects provide enzyme-free methods of synthesizing biopolymers.

Still other aspects provide improved methods for coupling nucleic acid oligonucleotides ("substrate oligonucleotides") into a longer oligonucleotide ("product oligonucleotide") where the sequence of the product oligonucleotide is governed by a preexisting DNA or RNA oligonucleotide ("template strand"). For example, a solution can be prepared containing a small molecule that intercalates the base pairs of a structure formed between a template strand and substrate oligonucleotides. A chemical or enzymatic method is used to couple the substrate oligonucleotides. The small molecule intercalator can be added to the reaction solution before or after the substrate and template oligonucleotides, or simultaneously with one of the oligonucleotides of the reaction.

In one aspect, the covalent linkage of mononucleotides and oligonucleotides into longer oligonucleotides is promoted by the close structural match between the intercalating molecule and the base pairs of the substrate oligonucleotides and the template strand. Thus, some aspects of the disclosure are generally applicable to improving nucleic acid template-directed synthesis by virtually any chemical means in which assembly of substrate oligonucleotides along a template strand is mediated by nucleotide base-pairing. Certain aspects of the present disclosure are compatible with nucleic acid polymers having natural backbones, but can also be used with analogous polymers having a non-natural backbone. Thus, aspects of the disclosure also have the ability to improve the synthesis of natural nucleic acid polymers using a synthetic non-natural analog of RNA or DNA as a template strand. Additionally, aspects of the disclosure can improve the coupling of non-natural oligonucleotides using natural RNA or DNA as a template strand. Other aspects of the present disclosure can also improve the synthesis of non-natural RNA-like oligonucleotides where a non-natural RNA-like oligonucleotide is used as a template strand.

Some of the molecules produced using the disclosed compositions and methods can be biologically active and of therapeutic value. In another aspects of the disclosure, the molecules produced by the disclosed methods exhibit molecular recognition abilities that are useful for diagnostic purposes.

A particular aspect provides a method of synthesizing a non-natural polynucleotide by combining in a fluid: a template, a plurality of non-natural nucleic acid subunits, and an intercalator. Adjacent non-natural nucleic acid subunits associated with the template are then ligated, for example without using a polymerase or ligase.

Another aspect provides a method of synthesizing a polynucleotide by combining in a fluid: a template comprising a non-natural backbone or a non-natural nucleotide, a plurality of nucleic acid subunits, and an intercalator; and ligating adjacent nucleic acid subunits associated with the template.

Still another aspect provides a method of synthesizing a biopolymer by combining a template, an intercalator, and biopolymer subunits in a fluid, wherein the intercalator has a structure according to Formula I:

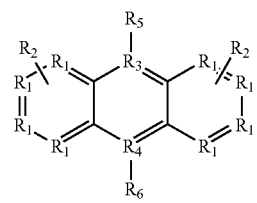

Formula I wherein each $R_1$ is independently C, S, O, or N;
$R_2$ is independently H, OH, N, carboxy, carbonyl, carbocyclo, substituted carbocyclo, cycloalkyl, substituted cycloalkyl, alkyl, substituted alkyl, aryl, substituted aryl, pyridine, pyrole, furan, alkyl substituted pyridine, alkyl substituted pyrole, alkyl substituted furan, heterocycle, or substituted heterocycle,
$R_3$ and $R_4$ are independently C, S, O, or N;
$R_5$ and $R_6$ are independently H, OH, N, carboxy, carbonyl, carbocyclo, substituted carbocyclo, cycloalkyl, substituted cycloalkyl, alkyl, substituted alkyl, aryl, substituted aryl, pyridine, pyrole, furan, alkyl substituted pyridine, alkyl substituted pyrole, alkyl substituted furan, heterocycle, or substituted heterocycle; and ligating the subunits together to form a biopolymer that is complementary to at least a portion of the template.

Another aspect provides a method of synthesizing a biopolymer by combining a template, an intercalator, and biopolymer subunits in a fluid, wherein the intercalator has a structure according to Formula II:

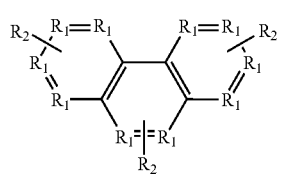

Formula II wherein each $R_1$ is independently C, S, O, or N; and
$R_2$ is independently H, OH, N, carboxy, carbonyl, carbocyclo, substituted carbocyclo, cycloalkyl, substituted cycloalkyl, alkyl, substituted alkyl, aryl, substituted aryl, pyridine, pyrole, furan, alkyl substituted pyridine, alkyl substituted pyrole, alkyl substituted furan, heterocycle, or substituted heterocycle; and ligating the subunits together to form a biopolymer that is complementary to at least a portion of the template.

Yet another aspect provides a method of synthesizing a biopolymer by combining a template, an intercalator, and biopolymer subunits in a fluid, wherein the intercalator has a structure according to Formula III:

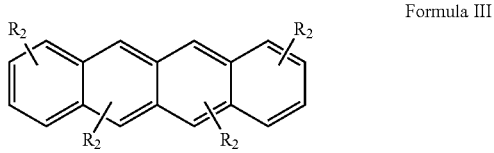

Formula III wherein $R_2$ is independently H, OH, N, carboxy, carbonyl, carbocyclo, substituted carbocyclo, cycloalkyl, substituted cycloalkyl, alkyl, substituted alkyl, aryl, substituted aryl, pyridine, pyrole, furan, alkyl substituted pyridine, alkyl substituted pyrole, alkyl substituted furan, heterocycle, or substituted heterocycle; and ligating the subunits together to form a biopolymer that is complementary to at least a portion of the template.

Another aspect provides a method of synthesizing a biopolymer by combining a template, an intercalator, and biopolymer subunits in a fluid, wherein the intercalator has a structure according to Formula IV:

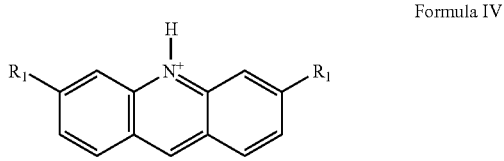

Formula IV wherein $R_1$ is independently H, OH, N, carboxy, carbonyl, carbocyclo, substituted carbocyclo, cycloalkyl, substituted cycloalkyl, alkyl, substituted alkyl, aryl, substituted aryl, pyridine, pyrole, furan, alkyl substituted pyridine, alkyl substituted pyrole, alkyl substituted furan, heterocycle, or substituted heterocycle; and ligating the subunits together to form a biopolymer that is complementary to at least a portion of the template.

Another aspect provides a method of selecting a biopolymer including the steps of generating a plurality of non-natural biopolymers having a random sequence of monomers flanked by predetermined sequences of monomers; selecting a subset of the plurality of the non-natural biopolymers based on binding affinity to a target; and synthesizing natural biopolymers by intercalator-meditated template-directed synthesis using the selected subset as templates.

Still another aspect provides a kit containing a template, biopolymer subunits, and an intercalator for performing intercalator-mediated template-directed synthesis. The kit optionally includes reagents, buffers, detectable labels, and instructions for performing the synthesis.

BRIEF DESCRIPTION OF THE DRAWINGS

FIG. 4A shows a primer oligonucleotide bound to a template strand (template strand is shown in gray). The substrate oligonucleotides are sufficiently short that there is no appreciable equilibrium of substrate oligonucleotides bound to the template strand. FIG. 4B shows the introduction of an intercalating molecule to the solution facilitates the formation of duplex structures between the template strand and substrate oligonucleotides with Watson-Crick complementary sequences. FIG. 4C shows chemical ligation used to join the backbones of substrate oligonucleotides aligned along the template strand to extend the primer the full length of the template strand. FIG. 4D shows the intercalator and unused substrate oligonucleotides can be removed from the reaction mixture as an early step in the process of product strand purification.

FIG. 5A shows two primer oligonucleotides are bound to a template strand (template strand is shown in gray). The "X's" on the outside ends of the two primers represent chemical modifications that prevent substrate ligation to these ends. Substrate oligonucleotides are present which are necessary for the synthesis of the product strand between the two primers. The substrate oligonucleotides are sufficiently short that there is no appreciable equilibrium of substrate oligonucleotides bound to the template strand. FIG. 5B shows the introduction of the intercalator molecule and reagents for backbone coupling results in the formation of a product strand that connects the two primers.

DETAILED DESCRIPTION

Figure 1:
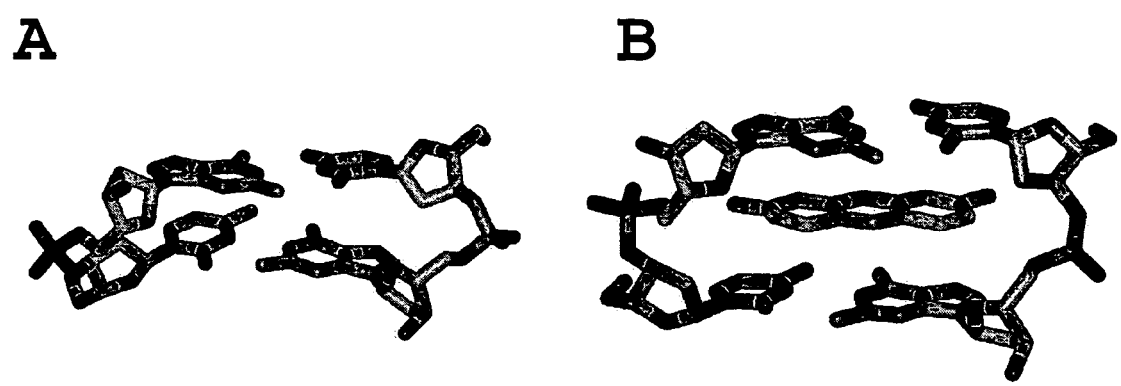
FIG. 1A is a diagram of the molecular structure of two base pairs from a high resolution structure of a B-form DNA double helix.
FIG. 1B is a diagram of the molecular structure of two base pairs intercalated by the small molecule proflavine.

1. Definitions:

A "biopolymer" is a polymer of one or more types of repeating units. Biopolymers are typically found in biological systems and particularly include polysaccharides (such as carbohydrates), peptides (which term is used to include polypeptides and proteins), glycans, proteoglycans, lipids, sphingolipids, known biologicals materials such as antibodies, etc. and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in hydrogen bonding interactions, such as Watson-Crick type, Wobble type and the like. Polynucleotides include single or multiple stranded configurations, where one or more of the strands may or may not be completely aligned with another. A "nucleotide" refers to a subunit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. A "biomonomer" references a single unit, which can be linked with the same or other biomonomers to form a biopolymer (e.g., a single amino acid or nucleotide with two linking groups one or both of which may have removable protecting groups).

The term "fluid" means a material continuum that is unable to withstand a static shear stress. Unlike an elastic solid which responds to a shear stress with a recoverable deformation, a fluid responds with an irrecoverable flow. Exemplary fluids include, but are not limited to, water, aqueous solutions, non-aqueous solutions, ionic salts, and other flowable material.

The term "biopolymer subunit(s)" means a biomonomer or group of two or more linked biomonomers. Exemplary biomonomers include, but are not limited to, nucleotides or nucleosides, amino acids, oligonucleotides, and polypeptides.

The term "nucleic acid subunit(s)" means a single nucleotide or nucleoside or a group of two or more nucleotides or nucleosides.

As used herein, the term "polynucleotide" generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompasses a polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including simple and complex cells, inter alia.

The term "oligonucleotide" refers to relatively short polynucleotides. Typically the term refers to single-stranded deoxyribonucleotides, but it can refer as well to single- or double-stranded ribonucleotides, RNA:DNA hybrids and double-stranded DNAs, among other compounds containing multiple nucleotides linked through phosphodiester bonds. The phosphodiester bonds are typically 5'-3' linkages between the deoxyribose or ribose sugars of adjacent nucleotides, which is the predominant mode of nucleotide coupling in natural DNA or RNA, respectively. The nucleotides of an oligonucleotide can be the naturally occurring ribonucleotides, rA, rC, rG and rU; deoxyribonucleotides, dA, dC, dG and dT; or other compounds in which the backbone and/or the base moieties differ from the standard nucleotides of DNA and RNA.

The term "non-natural" means not typically found in nature including those items modified by man. Non-natural includes chemically modified subunits such as nucleotides as well as biopolymers having non-natural linkages, backbones, or substitutions.

The term "non-natural backbone" means a covalent chemical linkage that couples together two or more nucleotides in a manner that is not identical to the naturally-occurring RNA or DNA phosphodiester backbones. Chemical deviations from the natural backbone can include, but are not limited to, chemical modification of a single site on the natural backbone or the replacement of a component of the backbone with a completely different chemical group. Methylation of the O2' site on the ribose sugar is an example of a chemical difference from the natural backbone that would constitute a non-natural backbone. Replacement of the ribose sugar with a hexose sugar and/or replacement of the phosphate group in DNA or RNA with a phosphorothioate group are also examples of non-natural backbones. Exemplary modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Representative oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof).

Some oligonucleotide backbones do not include a phosphorus atom therein and have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Some embodiments synthesize or use oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240.

In other embodiments, the disclosed methods and compositions may comprise modified oligonucleotides containing one or more substituted sugar moieties. Other modified oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$ $NH_2$, O($CH_2$)$_n$$CH_3$, O($CH_2$)$_n$O$NH_2$, and O($CH_2$)nON[($CH_2$)$_n$$CH_3$]$_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties and other substituents having similar properties. Another modification includes 2'-methoxyethoxy (2'-O—$CH_2CH_2OCH_3$, also known as 2'-O- (2-methoxyethyl) or 2'-MOE) (Martin et al. (1995) Helv. Chim. Acta, , 78, 486-504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, and 2'-dimethylaminoethoxyethoxy (also known in the art as 2'-O-dimethyl-aminoethoxy-ethyl or 2'-DMAEOE), i.e., 2'-O—$CH_2$—O—$CH_2$—N($CH_3$)$_2$.

Other modifications include 2'-methoxy (2'-O—$CH_3$), 2'-aminopropoxy (2'-O$CH_2CH_2CH_2NH_2$), 2'-allyl (2'$CH_2$—CH=$CH_2$), 2'-O-allyl (2'-O—$CH_2$—CH=$CH_2$)and 2'-fluoro (2'-F). The 2'-modification may be in the arabino (up) position or ribo (down) position. An exemplary 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

A further modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in U.S. Pat. No. 6,268,490 and WO 99/14226.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia of Polymer Science and Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases may be particularly useful for increasing the binding affinity of the oligomeric compounds of the disclosure. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

The term "substrate strand" (or substrate oligonucleotide) an oligonucleotide, with either a natural or non-natural backbone, of two nucleotide units or greater that is coupled to another substrate strand or mononucleotide during a template-directed synthesis reaction.

The term "template strand" means an oligonucleotide, with either a natural or non-natural backbone, that, by virtue of its nucleotide base sequence, guides the order of mononucleotide bases or substrate strands that are covalently coupled as part of a template-directed synthesis reaction.

The term "product strand" means an oligonucleotide, with either a natural or non-natural backbone, that is the product of a reaction in which shorter oligonucleotides or mononucleotides are covalently coupled to form a longer oligonucleotide with a nucleotide sequence that is determined by the template strand.

The term "intercalator" means a molecule with a planar component that inserts entirely, or partially, between adjacent monomers or a polymer, for example nucleotide bases of a nucleic acid structure.

The term "naturally-derived" when used in reference to a polymerase or a ligase enzyme indicates that the enzyme has an amino acid sequence that was originally isolated from a living organism. An enzyme is still considered to be naturally-derived if its amino acid sequence was subsequently mutated, evolved or truncated from the original naturally-occurring sequence.

The term "template-directed synthesis" in reference to biopolymer production, for example oligonucleotide production, refers to the assembly of substrate molecules on an existing template strand through non-covalent interactions which results in the product strand, upon covalent coupling of the substrates, having a sequence, for example a nucleotide sequence, that is governed by the template strand.

The term "intercalator-meditated template-directed synthesis" means using an intercalator to facilitate interactions between a monomer or substrate strand and a template, for example sequence specific interactions, during template-directed synthesis of a polymer. The intercalator can serve as a catalyst to promote sequence specific interaction between the template and the monomer.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMRA (5-Carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; AMCA (Aminomethylcoumarin); AMCA-X; Aminoactinomycin D; Aminocoumarin; Aminomethylcoumarin (AMCA); Anilin Blue; Anthrocyl stearate; APC (Allophycocyanin); APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy 505/515; Bodipy 530/10; Bodipy 542/563; Bodipy 18/568; Bodipy 564/517; Bodipy 576/589; Bodipy 581/591; Bodipy 630/650-X; Bodipy 650/665-X; Bodipy 665/676; Bodipy FI; Bodipy FL ATP; Bodipy FI-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson™; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP—Cyan Fluorescent Protein; CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3' DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DiD (DiIC18(5)); DIDS; Dihydrorhodamine 123 (DHR); DiI (DiIC18(3)); Dinitrophenol; DiO (DiOC18(3)); DiR; DiR (DiIC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer (CCF2); GFP (S65T); GFP red shifted (rsGFP); GFP wild type, non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1, low calcium; Indodicarbocyanine (DiD); Indotricarbocyanine (DiR); Intrawhite Cf; JC-1; JO-JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxadidole; Noradrenaline; Nuclear Fast Red; Nuclear Yellow; Nylosan Brilliant lavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; sgBFP™; sgBFP™ (super glow BFP); sgGFP™; sgGFP™ (super glow GFP); SITS; SITS (Primuline); SITS (Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC Tetramethyl-Rodaminelso ThioCyanate; True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1 ;YOYO-3 ,Sybr Green, Thiazole orange (interchelating dyes), semiconductor nanoparticles such as quantum dots, or caged fluorophore (which can be activated with light or other electromagnetic energy source) or a combination thereof.

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, etc. Lower alkyl groups, that is, alkyl groups of 1 to 6 carbon atoms, are generally most preferred. The term "substituted alkyl" refers to alkyl groups substituted with one or more groups, referably selected from aryl, substituted aryl, heterocyclo, substituted heterocyclo, carbocyclo, substituted carbocyclo, halo, hydroxy, alkoxy (optionally substituted), aryloxy (optionally subsituted), alkylester (optionally substituted), arylester (optionally substituted), alkanoyl (optionally substituted), aryol (optionally substituted), cyano, nitro, amino, substituted amino, amido, lactam, urea, urethane, sulfonyl, etc.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl. The term "substituted alkenyl" refers to alkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, etc.

The term "alkynyl" refers to straight or branched chain hydrocarbon groups having 2 to 12 carbon atoms, preferably 2 to 4 carbon atoms, and at least one triple carbon to carbon bond, such as ethynyl. The term "substituted alkynyl" refers to alkynyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, etc.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, etc., where optionally one or more pair of substituents together with the atoms to which they are bonded form a 3 to 7 member ring.

The terms "cycloalkyl" and "cycloalkenyl" refer to mono-, bi- or tri homocylcic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g. fluorene, tetrahydronapthalene, dihydroindene, and the like). The rings of multi-ring cycloalkyl groups may be either fused, bridged and/or joined through one or more spiro unions. The terms "substituted cycloalkyl" and "substituted cycloalkenyl" refer, respectively, to cycloalkyl and cycloalkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, etc.

The terms "carbocyclo", "carbocyclic" or "carbocyclic group" refer to both cycloalkyl and cycloalkenyl groups. The terms "substituted carbocyclo", "substituted carbocyclic" or "substituted carbocyclic group" refer to carbocyclo or carbocyclic groups substituted with one or more groups as described in the definition of cycloalkyl and cycloalkenyl.

The terms "halogen" and "halo" refer to fluorine, chlorine, bromine and iodine.

The terms "heterocycle", "heterocyclic", "heterocyclic group" or "heterocyclo" refer to fully saturated or partially or completely unsaturated, including aromatic ("heteroaryl") or nonaromatic cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranyl, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo [3.2.1]octane), azaspiroalkyls (such as 1,4 dioxa-8-azaspiro [4.5]decane), imidazopyridinyl (such as imidazo[1,5-a] pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl), and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclo" refer to heterocycle, heterocyclic and heterocyclo groups substituted with one or more, preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, etc., where optionally one or more pair of substituents together with the atoms to which they are bonded form a 3 to 7 member ring.

The term "alkanoyl" refers to alkyl group (which may be optionally substituted as described above) linked to a carbonyl group (i.e. —C(O)-alkyl). Similarly, the term "aroyl" refers to an aryl group (which may be optionally substituted as described above) linked to a carbonyl group (i.e., —C(O)-aryl).

Throughout the specification, groups and substituents thereof may be chosen to provide stable moieties and compounds.

The terms "including", "such as", "for example" and the like are intended to refer to exemplary embodiments and not to limit the scope of the present disclosure.

2. Template-Directed Synthesis

Certain embodiments of the disclosure provide compositions and methods for coupling monomers or subunits, for example polynucleotides (substrate strands) or mononucleotides, into a polymer, for example a polynucleotide or a longer oligonucleotide (product strand) in the presence or absence of an enzyme, for example a polymerase or ligase. In one embodiment the sequence of the product strand is dictated by a preexisting polymer, for example a DNA or RNA oligonucleotide (template strand). Generally, intercalators, including but not limited to proflavine, are used to facilitate aligning monomers on the template strand, for example by aligning the monomers according to sequence specific complementarity on the template strand. In one embodiment, the associations of monomers with a template are more frequent in the presence of an intercalator than in the absence of an intercalator. In another embodiment, the duration and/or stability of the association of monomers with a template are increased in the presence of a intercalator compared to associations in the absence of the intercalator. Once aligned, the monomers are covalently coupled or ligated to each other using a number of enzyme-free chemical procedures or using an enzyme such as a polymerase or ligase. Representative chemical ligation procedures include but are not limited to 1) methods that require addition of a water soluble coupling agent, such as carbodimmide, cyanoimidazole, or K3Fe(CN)6, to a solution containing the monomers, for example nucleic acids, to be coupled (Ferns et al., 1989; Kanaya and Yanagawa, 1986; Rubin et al., 1995); 2) methods in which one of the two monomers, for example, nucleic acids to be coupled has a high-energy leaving group on a terminal phosphate, such as the methyl imidazole (Inoue and Orgel, 1982; Kanavarioti et al., 1998); 3) and those methods in which the two monomers, for example, nucleic acids to be coupled are modified with different terminal groups that facilitate spontaneous covalent bond formation with each other, for example the use of a terminal phosphorothioate to form a covalent bond with an oligonucleotide that has an iodine or bromine atom to act as a leaving group during bond formation (Gryaznov et al., 1994; Xu and Kool, 1999). In one embodiment, a nucleic acid strand produced by template-directed synthesis has a sequence that is the Watson-Crick complement of its template strand.

Another embodiment provides a method for template-directed synthesis of nucleic acids in a fluid, for example in aqueous solution. The method includes providing a template strand with nucleotide base sequence information of interest and substrates in the form of oligonucleotides or mononucleotides that can be covalently coupled to form a product strand with a sequence determined by the template strand. The oligonucleotides or mononucleotides are aligned on the template strand using an intercalator such that the bases of the substrates form Watson-Crick, or other (e.g., Hoogsteen), base pairs with the bases of the template strand. Once aligned, substrate nucleic acids are ligated using a chemical procedure for the formation of a covalent bond between the oligonucleotides or mononucleotides aligned on the template strand.

In living systems, polymerase and ligase enzymes play a critical role in promoting the alignment of substrate mononucleotides and oligonucleotides, respectively, along template strands. The Watson-Crick hydrogen bonds between nucleic acid substrates and templates provide only part of the free energy necessary for the assembly of a substrate-template helix; additional non-covalent interactions between the polymerase or ligase enzymes and the template-substrate complex provide additional stability and selectivity to ensure correct Watson-Crick base pairing. Natural polymerases and ligases have evolved to contain nanometer-scale cavities that match the shape of a nucleic acid duplex with Watson-Crick base pairs. Thus, the cavity provided by polymerase and ligase enzymes is largely responsible for the fidelity in translation of sequence information from a template strand to a product strand. These same protein enzymes also act as catalysts for promoting bond formation between oligonucleotides or mononucleotides that are assembled along a template strand. The energy necessary to promote formation of the phosphodiester bond in natural nucleic acid replication systems is provided in the form of nucleotide triphosphates (e.g. dATP, dGTP, dCTP, dTTP).

Figure 2:
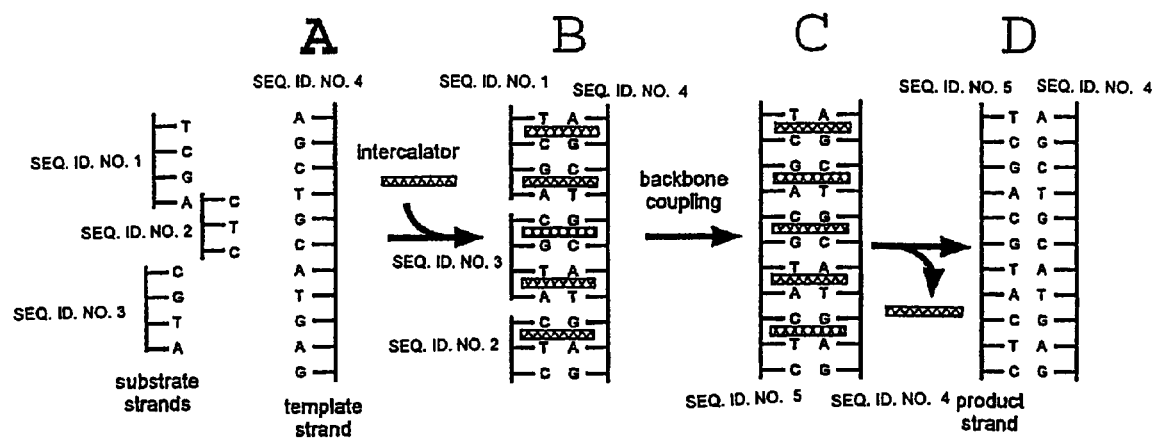
FIG. 2A is a schematic representation of an exemplary embodiment of intercalation-mediated template-directed synthesis showing a template strand in solution with substrate strands. The substrate strands are sufficiently short that the equilibrium amount of substrate strands bound to the template strand is extremely small.
FIG. 2B is a schematic representation showing that the addition of an intercalating molecule to the solution facilitates the formation of a duplex between the template strand and substrate strands with Watson-Crick complementary sequences.
FIG. 2C is a schematic representation showing chemical ligation used to join the backbones of substrate strands aligned along the template strand.
FIG. 2D is a schematic representation showing that the intercalator can be removed from the reaction mixture as an early step in the process of product strand purification.

Certain embodiments of the present disclosure provide compositions and methods to enable or improve the enzyme-free template-directed synthesis of biopolymers, for example nucleic acid oligonucleotides and related polymers, in aqueous solution using molecules that intercalate the monomers of the biopolymer, for example that intercalate bases of nucleic acid structures (FIG. 1). More specifically, a particular molecule is used in a template-directed synthesis reaction that intercalates between the base pairs of a non-covalent molecular assembly formed between a template strand and substrate oligonucleotides (FIG. 2). The non-covalent assembly of substrate and template strands by the intercalator can increase the stability of the assembly and thereby enhance reaction yield (FIG. 2). A chemical or enzymatic method is used to couple the substrate oligonucleotides of the template-substrate-intercalator complex to yield the product strand (FIG. 2). The intercalator molecules can be added to the solution before the substrate oligonucleotides, after the substrate strands, or after the addition of both the template strands and substrate strands to the reaction mixture. Molecules that interact with nucleic acid duplexes only through intercalation, as opposed to a combination of intercalation and backbone interactions, make contacts only with the bases and only through non-covalent interactions. These interactions include dipole-dipole interactions, dispersion interactions and interactions resulting from the hydrophobic effect. In a nucleic acid duplex, adjacent base pairs are stacked upon each other with a normal distance between the planes of the respective base pairs of 0.34 nm (FIG. 1). The insertion of an intercalator between two adjacent base pairs results in an increase in the normal distance between the planes of the intercalated base pairs from 0.34 nm to 0.68 nm (FIG. 1). The duplex structure accommodates this change in base pair separation by a local reduction in the twist of the helix. This increased separation of adjacent base pairs by untwisting of a duplex is possible because the distance between adjacent nucleotide bases along a nucleic acid backbone is approximately 0.68 nm.

Chemical methods for the template-directed synthesis of nucleic acids promise to be far more amendable to use with non-natural nucleic acid backbones and base analogs than enzymatic methods. However, not using naturally-derived polymerase or ligase enzymes necessitates the use of an alternate means for promoting the formation of covalent bonds between substrate oligonucleotides, as well as an alternate means for promoting the non-covalent alignment of substrate oligonucleotides and/or mononucleotides on a template strand. Decades of research in the area of nucleic acid template-directed synthesis has demonstrated that hydrogen bonding between the nucleotide bases of a template strand and substrate strands of less than six nucleotides is insufficient for high yield and high sequence fidelity template-directed synthesis. The use of an intercalating molecule to promote the noncovalent assembly of substrate oligonucleotides along a template strand overcomes obstacles of prior enzyme-free methods for nucleic acid template-directed synthesis.

Certain embodiments of the present disclosure use intercalating molecules to enhance the assembly of substrate strands along a template strand, which will facilitate covalent bond formation between substrates by any number of chemical methods. In one embodiment, the shape of the intercalator closely matches the shape of the Watson-Crick base pairs. In some embodiments, the intercalator need not make direct contact with any backbone atoms of the substrate, template or product strands to promote template-directed synthesis. Thus, one exemplary method of the present disclosure for improving template-directed synthesis is compatible with the natural backbone of nucleic acid polymers, but can also be used in template-directed synthesis reactions that utilize oligonucleotides with non-natural backbones. Other embodiments of the present disclosure can be used to improve the template-directed synthesis of oligonucleotides with a non-natural backbone on a natural nucleic acid template, the synthesis of oligonucleotides with natural backbones on a template with a non-natural backbone, or the synthesis of oligonucleotides with non-natural backbones on template strands with a non-natural backbone.

3. Intercalators

Exemplary intercalating molecules of the present disclosure include, but are not limited to, compounds having a planar, generally aromatic, more particularly polycyclic moiety that inserts into a polymer, for example a nucleic acid. The intercalator can comprise of a planar, fused polycyclic ring structure. A representative intercalator has the following structure:

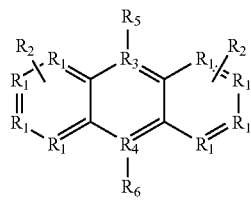

Formula I wherein each $R_1$ is independently C, S, O, or N;

$R_2$ is independently H, OH, N, carboxy, carbonyl, carbocyclo, substituted carbocyclo, cycloalkyl, substituted cycloalkyl, alkyl, substituted alkyl, aryl, substituted aryl, pyridine, pyrole, furan, alkyl substituted pyridine, alkyl substituted pyrole, alkyl substituted furan, heterocycle, or substituted heterocycle, $R_3$ and $R_4$ are independently C, S, O, or N;

$R_5$ and $R_6$ are independently H, OH, N, carboxy, carbonyl, carbocyclo, substituted carbocyclo, cycloalkyl, substituted cycloalkyl, alkyl, substituted alkyl, aryl, substituted aryl, pyridine, pyrole, furan, alkyl substituted pyridine, alkyl substituted pyrole, alkyl substituted furan, heterocycle, or substituted heterocycle.

It will be appreciated that the compounds of the described formula can have one or more double bonds as shown or can be completely saturated. Further, one of skill in the art will recognize that each $R_1$ can be substituted with $R_2$ as shown.

Figure 3:
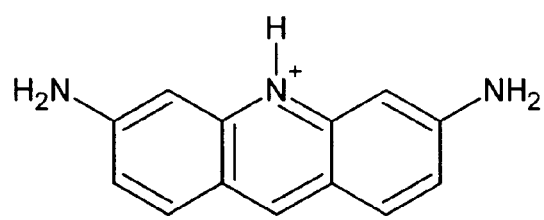
FIG. 3A is a diagram of the molecular structure of an exemplary intercalator, proflavine.
FIG. 3B is a space-filling model of the proflavine van der Waals surface.
FIG. 3C is the chemical structure of a Watson-Crick A•T base pair.
FIG. 3D is a space-filling model of the Watson-Crick A•T base pair. A black outline of the proflavine van der Waals surface is superimposed on the Watson-Crick base pairs to illustrate the close match between the shapes of these molecular structures.
FIG. 3E is the chemical structure of a Watson-Crick G•C base pair.
FIG. 3F is a space-filling model of the Watson-Crick G•C base pair. A black outline of the proflavine van der Waals surface is superimposed on the Watson-Crick base pairs to illustrate the close match between the shapes of these molecular structures
Figure 3:
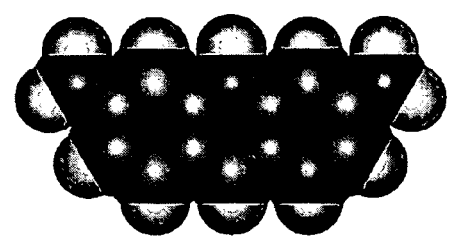
Figure 3:
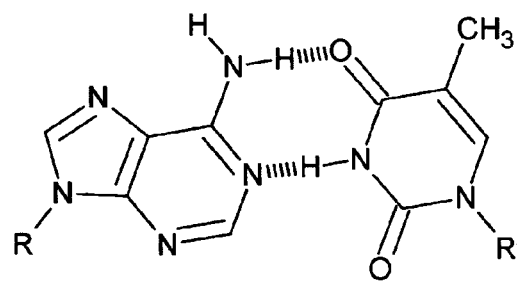
Figure 3:
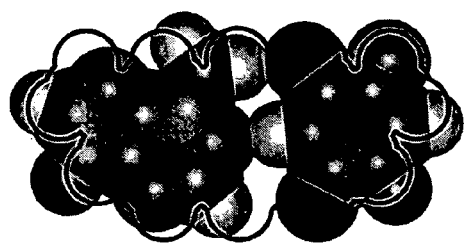
Figure 3:
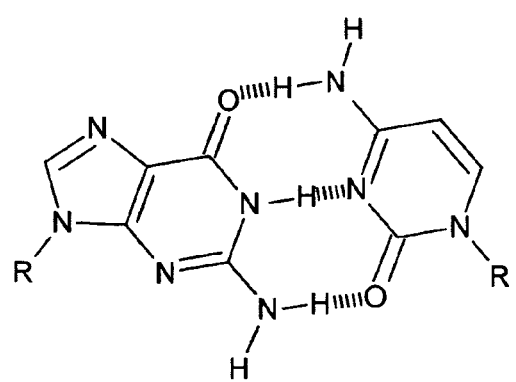
Figure 3:
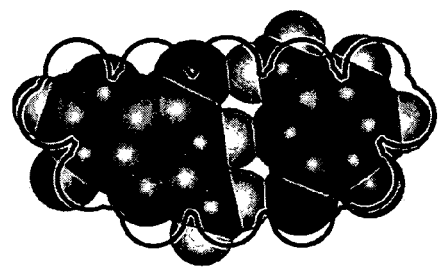

A representative intercalator of formula I includes, but is not limited to proflavine (also known as 3,6,-diaminoacrydine) or derivatives thereof. A van der Waals space-fill model of proflavine is shown in FIG. 3. The two-dimensional projection of this model for proflavine defines a surface that is a reasonable approximation of the van der Waals surface of proflavine. Space-filling models of the A•T and G•C Watson-Crick base pairs are also shown in FIG. 3. A coplanar superimposition of the outline of the proflavine van der Waals surface on the Watson-Crick base pair models illustrates the excellent match between these three surfaces (FIG. 3). It has been long appreciated that the structure and van der Waals surface of the two Watson-Crick base pairs are very close. It is this structural similarity between the two Watson-Crick base pairs that allows the natural polymerases to recognize the correct base pairing during information transfer. Likewise, an intercalator with a molecular surface that matches one Watson-Crick base pair will also match the other base pair. The simple coplanar superposition of the proflavine surface on the A•T base pair surface reveals that approximately 90% of the Watson-Crick base pair surface is matched by the proflavine surface (FIG. 3). In the present disclosure, it is considered to be of substantial importance that the surface of the intercalator, used to promote template-directed synthesis, closely match the surface of the base pairs to be formed between the bases of the template and substrate strands.

Another embodiment provides an intercalator having the formula

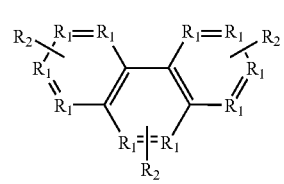

Formula II wherein each $R_1$ is independently C, S, O, or N; and $R_2$ is independently H, OH, N, carboxy, carbonyl, carbocyclo, substituted carbocyclo, cycloalkyl, substituted cycloalkyl, alkyl, substituted alkyl, aryl, substituted aryl, pyridine, pyrole, furan, alkyl substituted pyridine, alkyl substituted pyrole, alkyl substituted furan, heterocycle, or substituted heterocycle.

It will be appreciated that the compounds of the described formula can have one or more double bonds as shown or can be completely saturated. Further, one of skill in the art will recognize that each $R_1$ can be substituted with $R_2$ as shown.

Still another embodiment provides an intercalator having of the formula:

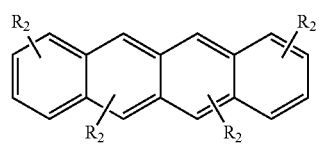

Formula III wherein $R_2$ is independently H, OH, N, carboxy, carbonyl, carbocyclo, substituted carbocyclo, cycloalkyl, substituted cycloalkyl, alkyl, substituted alkyl, aryl, substituted aryl, pyridine, pyrole, furan, alkyl substituted pyridine, alkyl substituted pyrole, alkyl substituted furan, heterocycle, or substituted heterocycle.

It will be appreciated that the compounds of the described formula can have one or more double bonds as shown or can be completely saturated. Further, one of skill in the art will recognize that each ring carbon can be substituted with $R_2$ as shown.

Another embodiment provides an intercalator having of the formula:

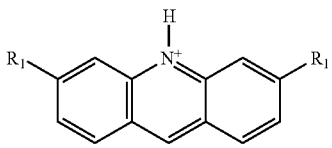

Formula IV wherein $R_1$ is independently H, OH, N, carboxy, carbonyl, carbocyclo, substituted carbocyclo, cycloalkyl, substituted cycloalkyl, alkyl, substituted alkyl, aryl, substituted aryl, pyridine, pyrole, furan, alkyl substituted pyridine, alkyl substituted pyrole, alkyl substituted furan, heterocycle, or substituted heterocycle.

It will be appreciated that the compounds of the described formula can have one or more double bonds as shown or can be completely saturated.

Amsacrine, 9-Aminoacridine-4-carboxamide, Daunomycin, triostine A and echinomycin, acridine orange, 9-amino acridine, ethidium, ellipticine, actinomycin, and DAPI are additional suitable intercalators.

The disclosed intercalators or derivatives thereof, are typically present in a ligation reaction in amounts ranging from about 1 nM to about 1 mM, about 100 nM to about 170 µM, typically from about 500 nM to about 500 µM, and more typically from about 1 µM to about 300 µM, even more typically from about 10 to 200 µM. Specific concentrations of intercalator in a given ligation reaction may vary depending on ligation conditions such as ionic strength, temperature, and the concentration of template and subunits to be ligated. Generally, the concentration of template strand to intercalator is greater than 1:1, and can be in the range of 1:1 to about 1:500, more typically about 1:200.

4. Ligation Chemistry

Embodiments of the present disclosure encompass a variety of ligation chemistries. For example, in one embodiment substrate monomers, for example mononucleotides, to be ligated are prepared with a methyl-imidazole-activated phosphate on the 5' position of ribose. The preparation of methyl-imidazole-activated mononucleotides has been described previously (Lohraian and Orgel, 1978 which is incorporated by reference herein in its entirety). A backbone linkage will form spontaneously when the methyl-imidazole-activated end of a substrate is brought into close proximity to an unmodified end of another substrate oligonucleotide with the aid of intercalators and a template strand. This particular embodiment of the disclosure will be useful for applications that require the template-directed synthesis of oligonucleotides that contain only natural phosphodiester linkages, as the methyl-imidazole modification acts as a high-energy leaving group that promotes a natural phosphodiester bond formation between the terminal phosphate of a mononucleotide and the 3'-terminal OH group of an oligonucleotide.

In another embodiment of the disclosure, chemical modifications to the termini of oligonucleotide substrates are made, prior to the template-directed synthesis reaction that will promote the formation of a covalent bond between two oligonucleotides (FIG. 2). In the presence of a template strand, the intercalator greatly increases the equilibrium amount of the non-covalent assembly between the template strand and the substrate strands (FIG. 2). The chemical modifications at the ends of the oligonucleotide substrates are then responsible for creating a covalent bond to produce the product strand (FIG. 2). As an example of this particular embodiment of the disclosure, the chemistry used to covalently couple substrate strands can be the 5'-iodine/3'-phosphorothioate chemistry developed by Kool and coworkers (Xu and Kool, 1999). In this chemical ligation procedure, one substrate oligonucleotide is prepared with an iodine atom substituted for a hydrogen atom on the 5' position of the 5'-terminal deoxyribose sugar. A second substrate oligonucleotide is prepared with a phosphorothioate group on the 3' position of the 3'-terminal deoxyribose sugar. The assembly of two substrates such that the 3'-nucleotide of a phosphorothioate-modified oligonucleotide is in close proximity to the 5'-nucleotide of iodine-modified oligonucleotide leads to formation of a phosphorothioate backbone linkage that is analogous to the natural phosphodiester linkage. One skilled in the art of nucleic acid technology can prepare the oligonucleotide template and substrate strands required for this reaction using an automated DNA synthesizer and commercially available reagents. A protocol can be followed that is identical or similar to that reported previously by Kool and coworkers (Xu and Kool, 1999), with the additional step of an intercalator being added to the reaction mixture to enhance the stability of the template-substrate reaction complex.

The progress of an intercalator-enhanced template-directed reaction can be followed using a number of techniques familiar to those skilled in the art. For example, a portion of a reaction can be subjected to polyacrylamide gel electrophoresis (PAGE) under conditions that denature nucleic acid secondary structures (Beaucage et al., 2000). Nucleic acid molecules subject to electrophoresis in a polyacrylamide gel under denaturing conditions move through the gel matrix at rates that depend upon the length of the nucleic acid strand. Thus, knowledge of the substrate, template and expected product oligonucleotide lengths will allow one skilled in the art to identify nucleic acid bands in a denaturing polyacrylamide gel that correspond to the substrate, product and template oligonucleotides. Changes in the amount of oligonucleotide in particular bands, both in the appearance of new bands and the change in the intensity of existing bands, can be used to follow the consumption of substrates and the formation of product strands. To visualize the oligonucleotides in a polyacrylamide gel, the gel can be stained with a dye (e.g. ethidium bromide) that allows detection of nucleic acids by UV excitation and fluorescence imaging (Beaucage et al, 2000). Alternatively, one or more of the substrate strands can be labeled with a radioactive phosphate group, such as $^{32}P$-phosphate, on a terminal end of an oligonucleotide that would not interfere with product formation during the ligation reaction (Beaucage et al., 2000). When radioactive labeling is used as a detection method, DNA bands in a polyacrylamide gel are detected by either exposing X-ray film to the gel, or by the use of an imaging plate in which radioactive decay induces phosphorescence that can be imaged by a commercially available phosphorescence plate imager.

In another embodiment of the disclosure, the reagents required to chemically ligate substrate oligonucleotides are not covalently bound to either of the substrates, but are added as separate reagents to the reaction mixture. The nucleic acid coupling chemistry that utilizes 1-(3-dimethylaminopropyl)-3-ethylcarbodiimide (GDI) for chemical activation of nucleic acid substrates (Shabarova et al., 1981; Shabarova et al., 1983; von Kiedrowski, 1986) serves as an example of this embodiment of the disclosure. For coupling using GDI, the substrate oligonucleotides to be ligated are prepared with a phosphate group on the 5' end of one substrate and an OH group at the 3' end of the second substrate. The 5' phosphate can be added to the oligonucleotide using a standard enzymatic or chemical protocol (Beaucage et al., 2000). The substrate oligonucleotide on which the phosphate group is to be present is chosen such that when the two substrates are aligned on the template strand, the 5'-phosphate group of substrate will be adjacent to the 3'-end of the second substrate oligonucleotide. The assembly of these substrates on the template strand is facilitated by the addition of an intercalator. The coupling of substrates is achieved by the subsequent addition of GDI according to a published protocol (Shabarova et al., 1981; Shabarova et al., 1983; von Kiedrowski, 1986).

Depending upon the specific application, the ultimate use of oligonucleotides prepared by the current disclosure may require separation of product strands from the intercalator. Separation of intercalators from oligonucleotides in a reaction mixture is facilitated by the substantial difference between the molecular weight, size, and chemical properties of intercalators and oligonucleotides. Separation of oligonucleotides and intercalators can be accomplished by several methods familiar to those skilled in the art, including, but not limited to: reverse-phase HPLC; cation-exchange chromatography, size exclusion chromatography and membrane dialysis.

In one embodiment of the present disclosure, more than two oligonucleotides are assembled together, with the aid of intercalators, on a single template strand to allow the synthesis of a product strand that is the full length of the template strand (FIG. 2). In a particular application of this embodiment, the sequence of the template strand may not be known, in which case a set of oligonucleotides is added to the reaction mixture that, regardless of template sequence, contains a subset of oligonucleotides that can be ligated together to create any possible sequence that is the Watson-Crick complement of the template strand. The chemical ligation method used for coupling the backbones of multiple intercalator-assembled oligonucleotides can be any of the chemical ligation methods known to those skilled in the art that proves compatible with nucleic acid intercalation.

One advantage of the current disclosure is the length of oligonucleotides that can be ligated together along a template strand is decreased substantially in comparison to existing methods for template-directed synthesis. This is important in regards to template-directed synthesis using multiple short oligonucleotides as substrates to produce a significantly longer product strand. The ability to use shorter oligonucleotides greatly reduces the number of substrate oligonucleotides necessary in a mixture that are required to insure generation of a product strand when using a template strand of unknown sequence. For example, if a nucleic acid polymer 120 bases in length is to serve as a template in an enzyme-free chemical ligation reaction in which an intercalator is not used, the shortest oligonucleotide that can feasibly serve as substrates under typical reaction conditions and protocols are of approximately six nucleotides in length (Pritchard and Southern, 1997). This limit on oligonucleotide length comes about because oligonucleotides shorter than hexanucleotides do not bind with sufficient equilibrium to a template strand to allow appreciable product formation. The set of hexanucleotides required to insure the ability to produce all possible sequences of 120 nucleotides in length will require 4096 oligonucleotide substrates, which corresponds to the total number of possible hexanucleotide sequences ($4^6$=4096). If the use of an intercalator can reduce the length of oligonucleotides required for template-directed synthesis from six to three bases in length, then only 64 oligonucleotides will be necessary because there are only 64 possible trinucleotide sequences ($4^3$=64). Thus, a two orders of magnitude reduction in oligonucleotide preparation could be achieved by the use of an intercalator that allows reduction in oligonucleotide length from six to three bases. This improvement greatly increases the potential utility of enzyme-free template-directed synthesis in which chemical ligation is used to couple oligonucleotides.

In one embodiment of the disclosure, non-natural oligonucleotides are used as template strands for the synthesis of natural DNA oligonucleotide product strands. For example, modified RNA oligonucleotides that have a methyl modification on the 2'-oxygen of one or more ribose sugars of the oligonucleotide backbone can be used as template strands. The preparation of oligonucleotides with 2'-O-methyl modifications can be accomplished by one skilled in the art using an automated nucleic acid synthesizer and commercial reagents (Beaucage et al., 2000). The non-natural oligonucleotide template is mixed in a reaction solution with intercalators and short oligonucleotide substrate strands that are chemically activated such that they spontaneously couple to form a full-length product strand when aligned along a template strand. By using this embodiment of the disclosure, the sequence information of a non-natural oligonucleotide can be transferred to a natural oligonucleotide.

Figure 4:
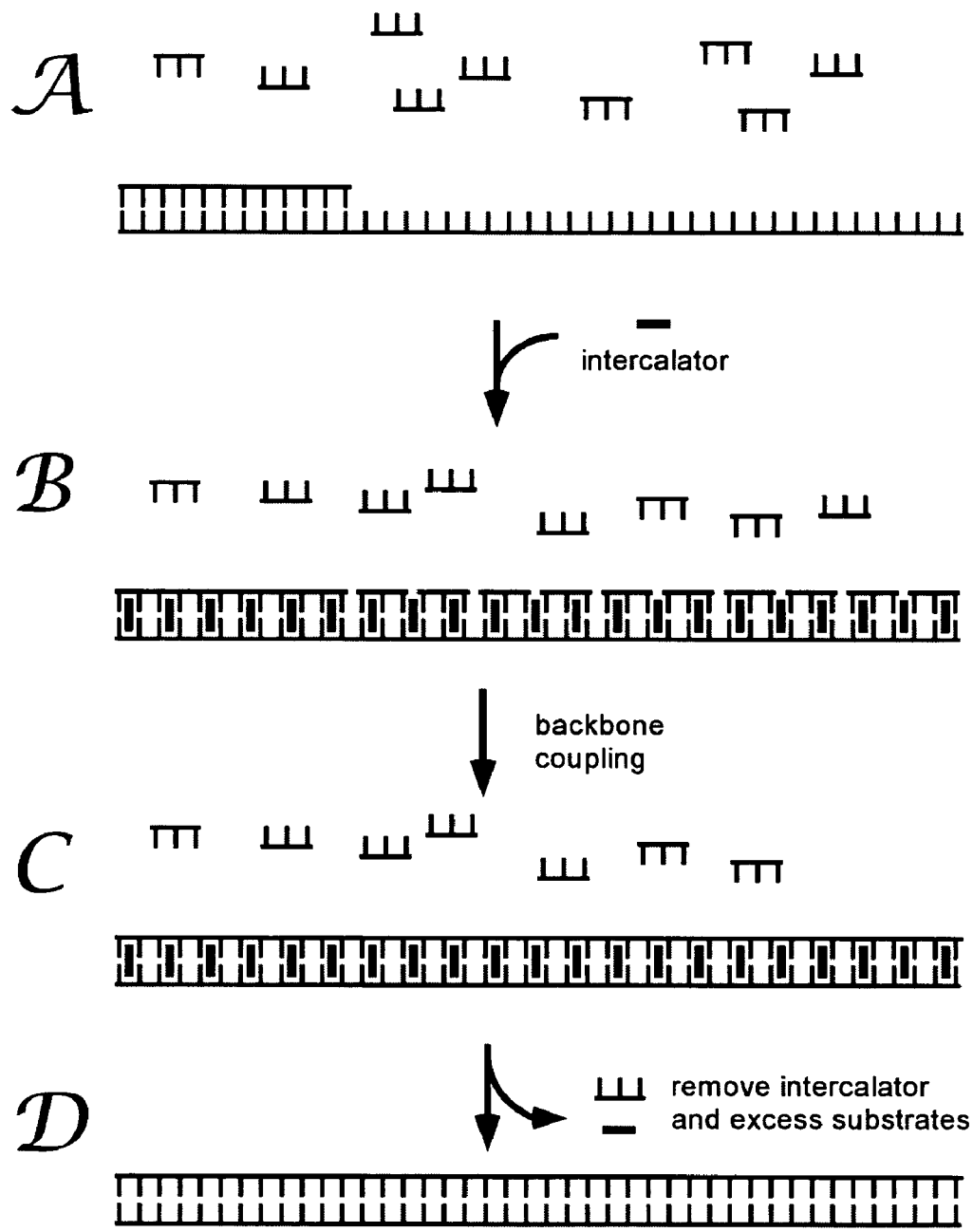
FIGS. 4A-D are a schematic representation of an exemplary embodiment of intercalation-mediated primer extension.
Figure 5:
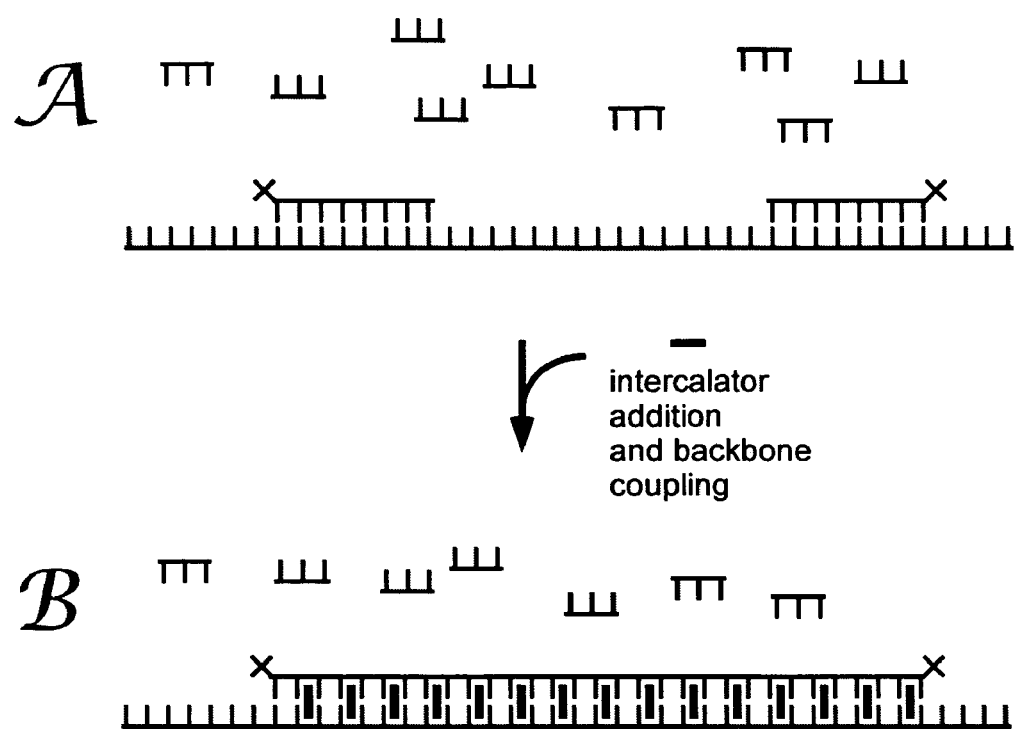
FIGS. 5A-B are a schematic representation of an exemplary embodiment of intercalation-mediated synthesis that is restricted to the region between two primer oligonucleotides.

In one embodiment of the disclosure, intercalation-mediated template-directed synthesis can be used for primer extension. This process is analogous to the process by which naturally-derived polymerases copy a template strand into a product. In this embodiment of the disclosure, an oligonucleotide with a specific sequence and length is bound to a complementary sequence site on a template strand (FIG. 4). The primer is of sufficient length that the equilibrium of binding is greatly favored at the reaction temperature. The oligonucleotide substrates that will serve as substrates for template-directed synthesis of the remaining length of the template strand are sufficiently short that the equilibrium concentration of two substrates bound at neighboring sites along the template strand is substantially smaller than the equilibrium concentration of substrate being bound next to the tightly-bound primer (FIG. 4). Both solution conditions, such as temperature and ionic strength, can be used in conjunction with intercalating molecules to create an equilibrium situation where there is an appreciable equilibrium of oligonucleotides bound directly adjacent to the primer. Existing chemical ligation methods can then be used in conjunction with intercalation-enabled template-directed synthesis to extend the primer the full length of the template strand (FIG. 4). As a modification of this embodiment, a second primer can be bound at the opposite end of the template strand such that the process of intercalation-enabled template-directed synthesis produces a complete polymer between the first and second primer (FIG. 5). This particular embodiment of the disclosure would be very useful for translating a series of template strands into product strands when the primer binding sites at the beginning and end of the template strands are identical for all template strands, but the sequences between the two primer sites are highly variable. Furthermore, this embodiment of the disclosure would be useful when a limited region of a template strand is desired to be translated into a product strand. In which case, primers would be used to limit the extent of the template strand that is translated to the region between the two primers. This would be accomplished by modifying the primers such that their ends that point outside the desired sequence are unable to be ligated to substrate oligonucleotides (FIG. 5).

In other embodiments, the subunits of a polymer to be synthesized can be ligated in the presence of or using an enzyme, for example, a ligase or polymerase. The enzyme can be bacterial, eukaryotic including, but not limited to mammalian, or genetically modified versions thereof. Suitable polymerases include, but are not limited to, *E. coli* DNA polymerase I (holoenzyme), *E. coli* large fragment of DNA polymerase I (Klenow fragment), Bateriophage T4 DNA polymerase, Bateriophage T7 DNA polymerase, modified Bacteriophage T7 DNA polymerase, reverse transcriptase, terminal transferase, and thermostable DNA polymerases such as Taq polymerase.

5. In vitro Selection

Since the discovery that RNA molecules fold into three dimensional objects, which can have catalytic properties the selection of RNA and DNA molecules with specific molecular recognition properties or catalytic capabilities has become a prime focus of research. These molecule are called ribozymes or DNAzymes. They can, like antibodies, bind specifically to small molecules and also larger proteins and they can bind to transition states and therefore stabilize them, which induces catalysis. DNA and RNA receptors able to bind cellular proteins with high specificity are called aptamers. If they are used inside a cell to bind a specific protein in a cellular environment they are termed intramers. One process of finding these molecules is called SELEX standing for: systematic evolution of ligands by experimental enrichment.

Figure 6:
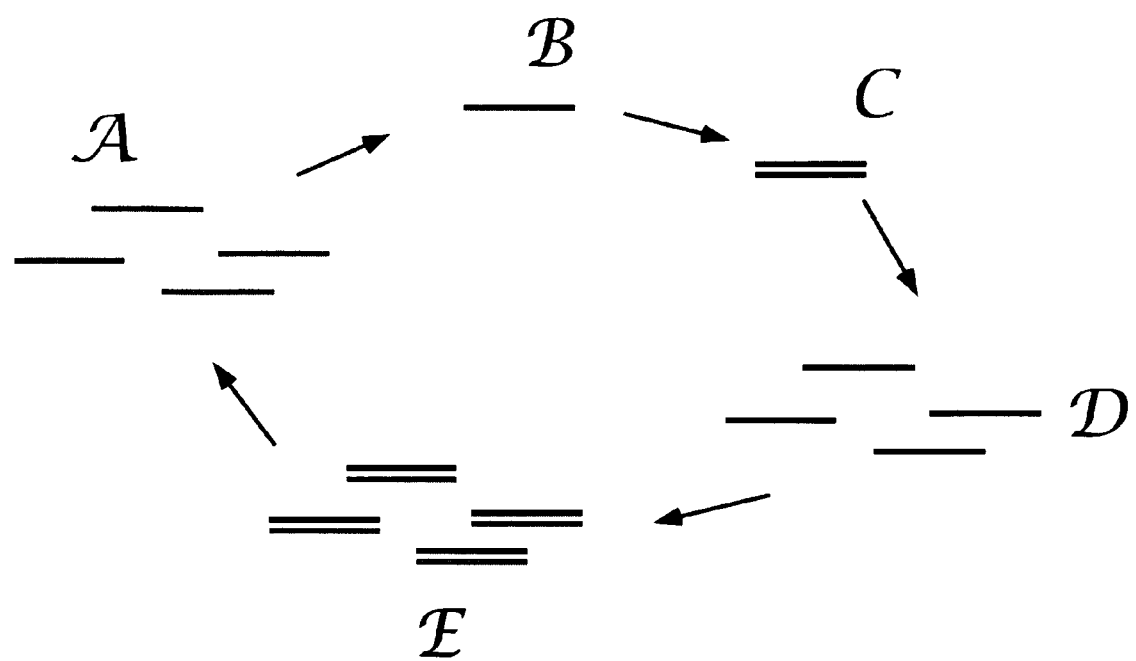
FIG. 6 is a schematic representation of an exemplary embodiment of a chemical procedure in which intercalation-mediated template-directed synthesis is used to selectively amplify nucleic acids with non-natural backbones that have sequences that exhibit a desired chemical or biological activity.

The ability of the present disclosure to enable synthesis of an oligonucleotide with a non-natural backbone using a template with a natural backbone provides a means to perform in vitro selection with non-natural oligonucleotides. In this embodiment of the disclosure, a sample of oligonucleotides, for example RNA, DNA, or a combination thereof, with a non-natural backbone and a segment of random sequence are prepared (FIG. 6A). To this end an RNA or DNA oligonucleotide synthesizer is programmed to couple not a single defined base but a mixture of all four bases. This randomized sequence is prepared in the middle to two defined sequences needed for primer recognition. A library having a mixture of $10^{15}$-$10^{16}$ individual oligonucleotide molecules is generally obtained.

The library can then be subjected to an activity or structure-based selection process that reduces the oligonucleotides to a subset that have a desired property (FIG. 6B). For example the library can be put onto an affinity column having a target molecule bound on a matrix. Suitable matrices include, but are not limited to, a polymer or hydrophobic silica gel. Those individual oligonucleotides of the library which have some affinity to the column and most likely to the compound bound to the surface will be retarded. These molecules are then eluted for example by increasing the salt concentration of the eluent. Fractions of eluate are collected from the affinity column containing non-natural oligonucleotides of interest.

This subset of non-natural biopolymers is then translated into DNA comprising natural nucleotides using intercalation-enhanced template-directed synthesis (FIG. 6C) and the DNA is then amplified using PCR (Batlett and Stirling, 2003) (FIG. 6D). The DNA is then translated back to the non-natural backbone by intercalation-enhanced template-directed synthesis (FIG. 6E).

A technique such as HPLC or polyacrylamide gel electrophoresis is used to separate the non-natural oligonucleotides from the DNA, resulting in non-natural oligonucleotides with an enrichment of sequences possessing the desired property (FIG. 6A). The non-natural oligonucleotides can then be subjected to the same selection procedure again. Repeating the entire cycle multiple times would allow the selection of molecules with non-natural backbones that have very specific properties. The selection criteria or conditions can be modulated for example by eluting with a more shallow salt gradient and collection of only the oligonucleotides that come off the column at rather high salt conditions. This will elute only the most powerful binding molecules. At the very end, the finally selected oligonucleotides are sequenced. It will be appreciated that non-natural oligonucleotides can be purified from natural oligonucleotides by contacting a heterogeneous sample with enzymes that degrade natural DNA or RNA including, but not limited to, nucleases.

The present disclosure will also be useful in facilitating the ligation of natural and non-natural nucleic acids that require ligation by chemical rather than enzymatic methods. Examples of when the present method may be useful, which are not meant to limit the scope of the disclosure, include applications in which current methods suffer low product yield due to: 1) differences in the chemical structure of the template and/or product backbone from the natural nucleic acid backbone; 2) differences in the chemical structure of the bases from the natural bases; 3) changes in the gross morphology of the nucleic acids, as in the ligation of non-duplex structures, such as triplexes, quadruplexes and branched junctions. In a preferred embodiment of the disclosure, the molecules produced using the disclosure are biologically active and used for a therapeutic application, or have desired physical properties for use as new materials. Exemplary therapeutics include, but are not limited to, antisense oligonucleotides, siRNA, and oligonucleotides that bind to specific epitopes of a protein or biomolecule.

6. Inhibitory Nucleic Acids

Other embodiments provide methods for producing inhibitory nucleic acids using intercalator-mediated template-directed synthesis. Inhibitory nucleic acids include, but are not limited to RNA interference (RNAi) technology, anti-sense DNA, D-RNAi (Messenger RNA-antisense DNA Interference), catalytic nucleic acids, and Peptide Nucleic Acids (PNAs). Anti-sense nucleic acids can be described as oligonucleotides characterized by short, gene-specific sequences of nucleic acids. Classical antisense compounds target specific strands of RNA within the cell to bind with, thus preventing translation of that RNA and thereby reducing levels of the corresponding protein.

6.1 RNA Interference (RNAi)

One embodiment of the disclosure, provides methods and compositions for synthesizing molecules for use in the RNAi pathway which will enhance the efficiency of RNAi technology, thus providing new therapeutic modalities that target specific genes in their associated diseases. Generally, the template nucleic acid will correspond to a target RNA to be down regulated. A complementary strand of RNA can be synthesized using intercalator-mediated template-directed synthesis. In one embodiment, the template RNA is a non-natural RNA. In another embodiment, the template RNA is a natural RNA and the syntheses complementary RNA comprises a modified backbone or non-natural nucleotide, or a combination thereof.

RNA interference (RNAi) silences gene expression in a sequence-specific manner by cleaving mRNAs containing short sequences that are closely homologous to a target sequence. Short double-stranded RNAs, known as small interfering RNAs (siRNA), are incorporated into an RNA-induced silencing complex that directs degradation of RNA containing a homologous sequence. RNAi was originally described in plants and in *Caenorhabditis elegans*, and has since been described in fungi, worms, flies, and mammals. RNAi acts via the targeted degradation of mRNAs containing homologous (often identical) sequences to introduced short oligonucleotides. In organisms such as *Drosophila* and *C. elegans*, RNAi can be induced by introducing long dsRNA complementary to the target mRNA to be degraded. Transfection of long dsRNA molecules (>30 nt) into most mammalian cells causes nonspecific suppression of gene expression, as opposed to the gene-specific suppression seen in other organisms. This suppression has been attributed to an antiviral response, which takes place through one of two pathways. To circumvent this, siRNAs are used to induce RNAi in mammalian cells and organisms.

In some embodiments, long double-stranded RNAs (dsRNAs; typically >200 nt) can be used to silence the expression of target genes in a variety of organisms and cell types (e.g., mammals, worms, fruit flies, and plants). Upon introduction, the long dsRNAs enter a cellular pathway that is commonly referred to as the RNA interference (RNAi) pathway. First, the dsRNAs get processed into 20-25 nucleotide (nt) small interfering RNAs (siRNAs) by an RNase III-like enzyme called Dicer (initiation step) in an ATP-dependent, processive manner. Then, the siRNAs assemble into endoribonuclease-containing complexes known as RNA-induced silencing complexes (RISCs), unwinding in the process. The siRNA strands subsequently guide the RISCs to complementary RNA molecules, where they cleave and destroy the cognate RNA (effector step). Cleavage of cognate RNA takes place near the middle of the region bound by the siRNA strand.

Other embodiments provide non-natural inhibitory nucleic acids synthesized by intercalator-mediated template-directed synthesis. There are several genes associated with cancer that are overexpressed to make cells resistant to native immunity, treatment, or normal senescence. Many of these genes are overexpressed in a wide array of tumors and are attractive candidates for RNAi silencing. The inhibitory nucleic acids of the present disclosure can be targeted to: the multidrug-resistance protein (MDR), which pumps chemotherapeutic drugs out of tumors; telomerase, which overcomes the chromosomal shortening that occurs with each cell division; Bcl-2, which makes cell resistant to caspase-mediated apoptosis. Other potential targets for silencing include but are not limited to the following growth factors or growth factor receptors that have oncogenic roles in specific tumors: IL-6 for multiple myeloma; Her-2 for breast cancer; viral oncogenes such as the HPV genes E6 and E7 for cervical cancer.

Viruses and other infectious agents may be targets of RNAi. These include but are not limited to influenza, severe acute respiratory syndrome, hepatitis B (HBV), hepatitis C (HCV), HIV, and intracellular pathogens (*Mycobacterium tuberculosis*). Certain bacteria are not typically amenable to RNAi silencing because of a lack of RNAi machinery, but the silencing of genes involved in the host immune response to life-threatening bacteria is possible. For example, reducing the expression of pro-inflammatory cytokines including, but not limited to, interleukin-1 (IL-1), tumor necrosis factor α (TNFα), may lesson the risk of septic shock.

siRNAs of the present disclosure can also be an effective therapeutic for neurodegenerative diseases caused by the overexpression of mutated genes or of proteins containing long polyglutamine stretches. The onset of neuronal cell death can be slowed or prevented by targeting the expression of the mutated allele or the polyglutamine sequence.

To date, injection and transfection of dsRNA into cells and organisms has been the main method of delivery of siRNA. And while the silencing effect lasts for several days and does appear to be transferred to daughter cells, it does eventually diminish. The present disclosure provides compositions and methods for synthesizing non-natural structural analogs of dsRNA and siRNA that are not susceptible to cellular enzymatic degradation, thus increasing the sustainability within the cell.

6.2 Anti-sense DNA

In another embodiment, the methods and compositions of the present disclosure can be used to generate molecules with anti-sense DNA properties. Antisense technology focuses on defeating diseases before the faulty proteins which cause them can even be formed. The production of these faulty proteins begins in the nucleus, with the DNA of the cell. In the nucleus the DNA forms pre-mRNA, which will leave the nucleus to enter the cytoplasm. In the cytoplasm this mRNA moves to a ribosome, where it is translated into amino acids. These amino acids are what make up the faulty proteins. Many traditional drugs target diseases by focusing on the faulty proteins themselves. Antisense goes a step further, by preventing the production of these incorrect proteins. The antisense DNA is inserted into the cell's cytoplasm. Next, the DNA of the nucleus codes the mRNA, which enters the cytoplasm of the cell. But instead of moving to a ribosome, this disease-producing mRNA connects to the strand of antisense DNA. So instead of producing proteins, the faulty mRNA is negated by the oligonucleotide. The disclosed methods and compositions are useful in synthesizing specific oligonucleotides or antisense DNA.

6.3 D-RNAi (Messenger RNA-antisense DNA Interference)

Another embodiment of the present disclosure provides applications using D-RNAi as a defense process against various diseases. D-RNAi is a novel posttranscriptional phenomenon of silencing gene expression by transfection of mRNA-aDNA hybrids. It has been shown to have long-term gene knockout effects and thus has applications for treating diseases including, but not limited to cancer and viral infections. D-RNAi is a process that introduces hybrids of mRNA and antisense DNA into mammalian cells, resulting in the specific silencing of genes homologous to the delivered mRNA-aDNA hybrid (Lin, 2001). The antisense DNA can be produced using the disclosed methods to provide enzyme resistance and to increase the effectiveness of the antisense DNA. In vivo and In vitro experiments have demonstrated the gene silencing effect of the D-RNAi process. The D-RNAi mechanism has been implicated in the following experiments: the experimental demonstration of bcl-2 oncogene knockout in human prostate cancer LNCaP cells, the developmental retardation of liver lobe formation by silencing catenin genes in chicken embryos, and the interference of viral gene expressions in HIV-infected CD4$^+$ T cells.

6.4 Peptide Nucleic Acid (PNAs)

Another embodiment provides methods of replicating PNAs using intercalator-mediated template-directed synthesis. The structure of a peptide nucleic acid (PNA) is similar to a DNA oligomer except that there is no phosphodiester backbone. PNAs are nucleic acid mimics that contain a pseudo-peptide backbone composed of charge neutral and achiral N-(2-aminoethyl) glycine units to which the nucleobases are attached via a methylene carbonyl linker. PNAs bind DNA and RNA with high specificity and selectivity. The binding affinity and selectivity of PNAs for nucleic acids can be modified by the introduction of stereogenic centers (such as D-Lys-based units) into the PNA backbone. PNA monomers can be easily synthesized into oligomers as long as 20 bases using protocols for standard peptide synthesis The methods of the present disclosure can be used in the synthesis of PNAs and associated complexes including, but not limited to, PNA-PNA, PNA-DNA, and PNA-RNA, and $PNA_2$-DNA. PNAs have proved to be useful molecules in DNA hybridization and antisense techniques. PNA complexes with DNA and RNA tend to be more stable than the related DNA-DNA or DNA-RNA duplexes, which are also very stable.

6.5 Targets for Anti-sense Therapeutics

As noted above certain embodiments provide methods and compositions for the synthesis of antisense oligonucleotides which offer the possibility of specific, rational, genetic-based therapeutics. Human cancer therapy is of particular interest in this field of research. Examples of cancer targets include, but are not limited to, bcl-2, BCR-ABL, C-raf-1, Ha-ras, c-myc, PKC, PKA, p53, and MDM2. Many genes specific to breast cancer that have been selected as targets for antisense therapy include, but are not limited to, HER-2/neu, PKA, TGF-Å, EGFR, TGF-ã, IGFIR, P12, MDM2, BRCA, Bcl-2, ER, VEGF, MDR, ferritin, transferrin receptor, IRE, C-fos, HSP27, C-myc, C-raf and metallothionein genes.

7. Microarrays

One embodiment provides a method of producing microarrays containing non-natural polynucleotides. For example, non-natural polynucleotides can be synthesized using the disclosed intercalator-mediated template-directed methods. The synthesized non-natural polynucleotides can be spotted onto a solid support to produce a microarray. Methods of fabricating microarrays are known in the art. In certain embodiments, the template is a non-natural polynucleotide having a predetermined sequence complementary to a target nucleic acid.

The disclosed microarrays use the ability of a given mRNA molecule to bind specifically to, or hybridize to, the DNA template from which it originated. By using an array containing many DNA or RNA samples, the expression levels of hundreds or thousands of genes within a cell can be detected by measuring the amount of mRNA bound to each site on the array. With the aid of a computer, the amount of mRNA bound to the spots on the microarray is precisely measured, generating a profile of gene expression in the cell.

There are two major application forms for the DNA microarray technology: 1) Identification of sequence (gene/gene mutation) in which probe cDNA (500~5,000 bases long) is immobilized to a solid surface such as glass using robot spotting and exposed to a set of targets either separately or in a mixture; and 2) Determination of expression level (abundance) of genes in which an array of oligonucleotide (20~80-mer oligos) or peptide nucleic acid (PNA) probes is synthesized either in situ (on-chip) or by conventional synthesis followed by on-chip immobilization. The array is exposed to labeled sample DNA, hybridized, and the identity/abundance of complementary sequences are determined.

The whole microarray process is based on hybridization probing, a technique that uses fluorescently labeled nucleic acid molecules as "mobile probes" to identify complementary molecules, sequences that are able to base-pair with one another. Base-pairing (i.e., A-T and G-C for DNA; A-U and G-C for RNA) or hybridization is the underlining principle of DNA microarray. An array is an orderly arrangement of samples. It provides a medium for matching known and unknown DNA samples based on base-pairing rules and automating the process of identifying the unknowns. An array experiment can make use of common assay systems such as microplates. In general, arrays are described as macroarrays or microarrays, the difference being the size of the sample spots. Macroarrays contain sample spot sizes of about 300 microns or larger and can be easily imaged by existing gel and blot scanners. The sample spot sizes in microarray are typically less than 200 microns in diameter and these arrays usually contains thousands of spots.

DNA microarray, or DNA chips can be fabricated by high-speed robotics, generally on, but not limited to glass or nylon substrates, for which probes with known identity are used to determine complementary binding, thus allowing massively parallel gene expression and gene discovery studies. The introduction of solid supports could greatly increase the range of applications of the disclosed method in conjunction with array-based methods. The supports could be, but are not limited to, glass microscope slides, silicon chips, or nylon membranes. An "array" can be defined as "to place in an orderly arrangement" or "an orderly arrangement." It is important that the gene sequences in a microarray are attached to their support in an orderly or fixed way, because researchers use the location of each spot in the array to identify a particular gene sequence. The spots themselves can be DNA, cDNA, or oligonucleotides. The present disclosure can be used to synthesize the specific "spots" as natural or non-natural DNA, cDNA, or oligonucleotides.

Microarrays produced using the disclosed methods can be used to investigate gene expression changes in angiogenesis, schizophrenia, type I diabetes, breast cancer, leukemia, neurological tumors. Personalized drugs, molecular diagnostics, and integration of diagnosis and therapeutics are examples of the long-term potential for microarrays produced using the disclosed methods.

8. Kits

Other embodiments provide kits for performing template-directed polymer synthesis. The kit typically includes monomers, such as mono- or polynucleotides or amino acids and peptides. The monomers can be labeled with a detectable label. Detectable labels are known in the art an include, but are not limited to, biotin, strepavidin, radioisotopes, fluorophores, phosphors, enzymes such as alkaline phosphatase, nanoparticles such as gold or silver particles of 100 nm or less in diameter, spin labels, molecular beacons, quenchers, and chromophores. The mono- or polynucleotide can be natural or non-natural. The polynucleotides typically include at least two natural or non-natural nucleotides. In one embodiment, the polynucleotides have a non-natural backbone. The kit also includes an intercalator as disclosed herein. Generally, the intercalator is a planar, polycyclic molecule, or a compound that contains a planar moiety capable of inserting between monomers of a polymer. The kit also contains ligation reagents. The ligation reagents include, but are not limited to, reagents for chemical ligation or enzymatic ligation as disclosed herein. Representative chemical ligation reagents include 1-(3-dimethylaminopropyl)-3-ethylcarbodiimide (GDI). Enzymatic reagents include polymerases, ligases, or combinations thereof. Buffers, co-factors, chelators, detectable labels and other reagents can also be included. The kit can also contain instructions for synthesizing non-natural polynucleotides from natural templates or instructions for synthesizing natural polynucleotides from non-natural templates.

EXAMPLES

Example 1

For example, the present disclosure could be used in an enzyme-free template-directed ligation reaction that would, in the absence of an intercalator, yield too little product to be of any practical purpose.

The utility of the present disclosure in a template-directed ligation reaction is demonstrated by measuring the amount of product strand that results from the coupling of the trinucleotide $(dT)_3$ to the tetranucleotide $(dT)_4$ on a $(dA)_{16}$ template in the presence and absence of the intercalator proflavine (FIG. 1). The product of this ligation reaction contains a single phosphorothioate linkage. Thus, the backbone of the product strand is not strictly DNA, like the template strand. However, the product strand backbone is an extremely close analog of DNA.

Synthesis and Purification of Oligonucleotides.

Substrate oligodeoxynucleotides were synthesized on a one micromole scale on an Expedite model 8909 synthesizer using standard phosphoramidite coupling chemistry. The 3'-phosphorothioate-$(dT)_3$ oligo synthesis was carried out on a 3'-phosphate controlled pore glass support (Glen Research, Sterling, Va.) where the oxidation reagent that would normally be added during the first nucleotide coupling cycle was replaced by a sulfurizing reagent (Glen Research). The remaining synthesis and deprotection steps were standard DNA nucleotide coupling cycles. The 5'-iodo-$(dT)_4$ substrate oligo was synthesized using the commercially available 5'-iodothymidine phosphoramidite reagent (Glen Research). Cleavage of iodine-containing strand from the CPG support was accomplished by incubation in concentrated ammonium hydroxide for 2 h at room temperature. No further deprotection was required for the 5'-iodo-$(dT)_4$ substrate. Substrate oligonucleotides were purified by reverse phase HPLC on a C18, semi-preparative column. Template DNA, $(dA)_{16}$, was synthesized on the automated synthesizer, deprotected by incubation in ammonium hydroxide at 1° C. for 18 h. Following evaporation of ammonium hydroxide on a concentrating centrifuge, $(dA)_{16}$ was purified from deprotecting groups and truncation products by passage over a 1 m G-15 column (Pharmacia). Stock solutions of DNA molecules were prepared by resuspending freeze-dried purified samples of each oligonucleotide in 1 ml of deionized HiO. The concentrations of DNA stock solutions were determined spectrophotometrically based upon sample absorption at 260 nm.

Proflavine Stock Preparation

Proflavine (hemisulfate salt) was purchased from Sigma. Stock solutions of 100 µM to 10 mM proflavine were prepared by dissolving solid proflavine sulfate in deionized $H_2O$. Concentrations of stock solutions were determined by UV-Vis is spectroscopy using the extinction coefficient: $\epsilon_{444}=38,900$ $M^{-1}$ $cm^{-1}$.

Isotope Labeling of DNA

Substrate 3'-phosphorothioate-$(dT)_3$ was radioactively labeled with $^{32}P$-phosphate at the 5'-end to allow monitoring of product formation. End labeling was accomplished by diluting 3'-phosphorotioate-$(dT)_3$ from a stock solution to 10 µM strand in 100 µl of T4 polynucleotide kinase buffer (New England Biolabs, Beverly, Mass.). 10 units of T4 polynucleotide kinase (New England Biolabs) were added to the buffered DNA solution. 3 µl γ-$^{32}P$-ATP (ICN, Costa Mesa, Calif.), 10 µCi/µl, was then added to the solution. The kinase reaction mixture was allowed to incubate at 37° C. for 30 mm.

Ligation Reactions

Reactions were carried out in 100 µl volumes in a buffer containing 10 mM Tris buffer (pH 8.2); 10 mM NaCl; 100 mM 2-mercaptoethanol. The substrate 5'-iodo-$(dT)_4$, the substrate $^{32}P$-labeled-3'-phosphorotioate-$(dT)_3$, and the template $(dA)_{16}$ were added to the reaction buffer to a final concentration for each of 1.0 µM in strand. The presence of 2-mercaptoethanol in the reaction buffer prevented dimerization of the 3'-phosphorothioate-$(dT)_3$ substrate by reducing disulfide bond formation. To each of a series of identical reaction mixtures, the intercalator, proflavine, was added to final concentrations from 10 to 200 µM. The exact intercalator concentrations investigated are shown on FIG. 7. Ligation reactions were incubated for 24 h at 4° C. and then stopped by plunging reaction test tubes into liquid nitrogen and freeze-drying.

Polyacrylamide Gel Electrophoresis

Freeze-dried reaction samples were resuspended in 50 µl of a 7 M urea solution and loaded on to a 40 cm×50 cm, denaturing 30% polyacrylamide gel (19:l::acrylamide:bi-sacrylamide). As oligonucleotide length standards, a sample containing $^{32}P$-end-labled $(dT)_8$, $^{32}P$-end-labled $(dT)_7$ and $^{32}P$-end-labled $(dT)6$ were loaded in gel lanes flanking the reaction samples. Polyacrylamide gels were subject to electrophoresis at a constant power of 60 W for 6 hours.

Analysis of Product Yield by Proflavine-enhanced Temple-directed Synthesis

The relative yield of $(dT)_7$ product for each reaction was determined by imaging the polyacrylamide gel on a Fuji PhosphorImager and quantifying the integrated intensity of gel bands in each lane that corresponded to the $(dT)_7$ ligation product using the software package Image Gauge V3.12. Background correction was accomplished by subtracting from all reaction samples the integrated intensity of an area in a control lane run with only $^{32}P$-end-labeled $(dT)_3$.

Figure 7:
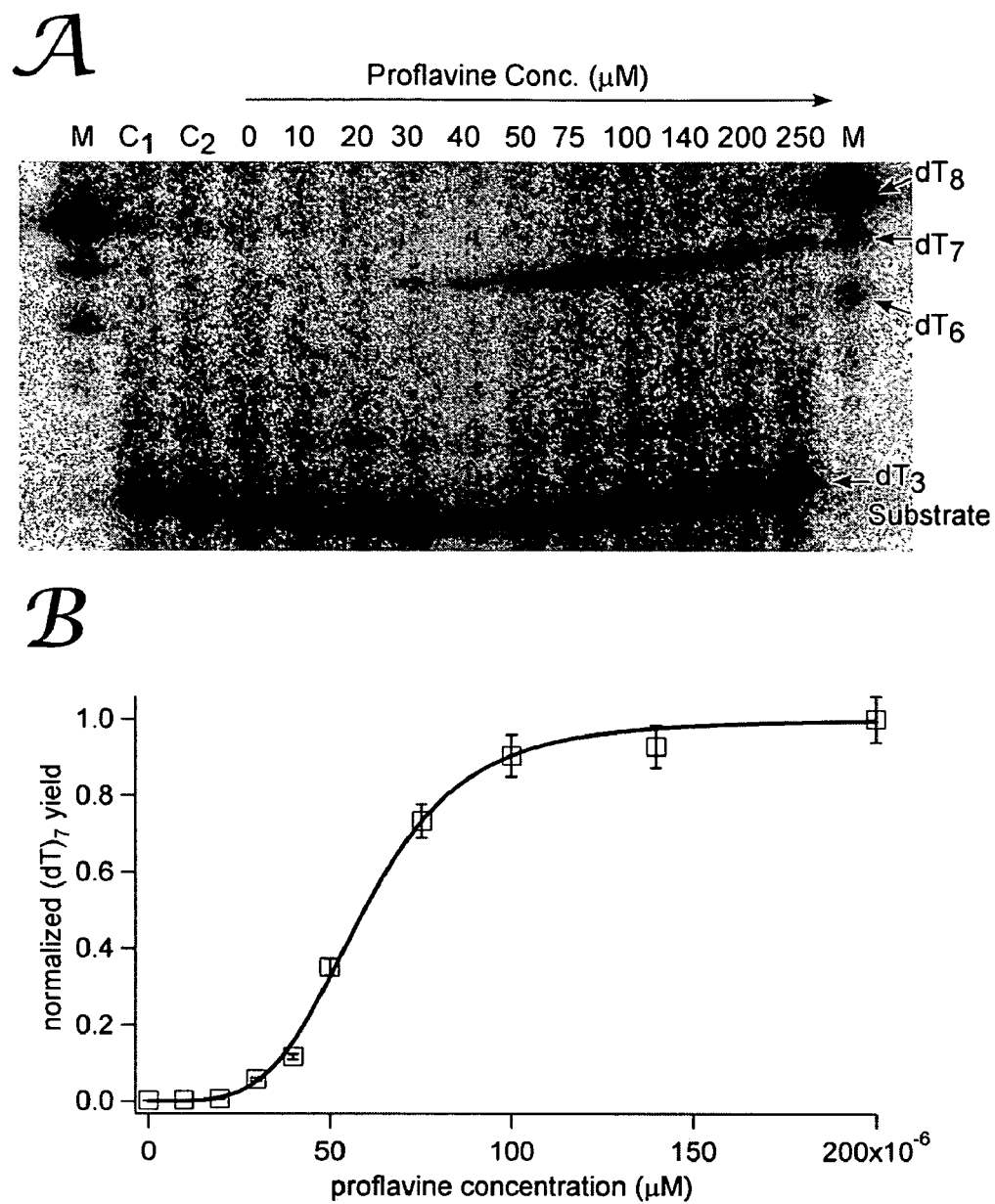
FIG. 7A is an autoradiography image of a polyacrylamide gel run with a number of intercalation-mediated ligation experiments using 3'-phosphorothioate-$(dT)_3$ and 5'-iodo-$(dT)_4$ as substrates, the DNA template $(dA)_{16}$, and the small molecule proflavine as an intercalator.
FIG. 7B is a line graph showing $(dT)_7$ product yield as a function of proflavine concentration.

A polyacrylamide gel of this set of experiments demonstrates that product yield is enhanced by the presence of proflavine (FIG. 7). A plot of integrated intensities for product bands as a function of proflavine concentration further illustrates that the template-directed synthesis of $(dT)_7$ is enhanced in a cooperative manner with respect to proflavine concentration. Maximum yield was obtained at a concentration of 200 µM proflavine (FIG. 7). This maximum yield corresponds to approximately a 1000-fold increase in product formation with respect to the control reaction that contains all components of the proflavine ligation reactions, except proflavine (Table 1).

TABLE 1

$(dT)_7$ yield as a function of reaction components.[a]

| substrates 3'-PO$_3$S-dT$_3$; 5'-I-dT$_4$ | template dA$_{16}$ | Proflavine concentration | $(dT)_7$ yield[b] |
|---|---|---|---|
| + | − | 0 | <20 |
| + | + | 0 | <20 |

TABLE 1-continued (dT)₇ yield as a function of reaction components.[a]

| substrates 3'-PO₃S-dT₃, 5'-I-dT₄ | template dA₁₆ | Proflavine concentration | (dT)₇ yield[b] |
|---|---|---|---|
| + | − | 140 μM | ~100 |
| + | + | 140 μM | 13,917 |

[a]Details of experimental conditions for the data of this table are given in Example 1.
[b]Product yield units correspond to integrated radioactivity intensities of (dT)₇ bands in a polyacrylamide gel.

The example given is to illustrate the disclosure and is not intended to limit the claims of the disclosure in any manner. One skilled in the art will appreciate from reading this disclosure that various changes in form and detail can be made without departing from the true scope of the disclosure.

Example 2

In this example, a template with an RNA backbone is used to guide the assembly of substrate oligonucleotides to yield a product strand with a DNA backbone that contains a single phosphorothioate linkage.

Synthesis and Purification of Oligonucleotides

The RNA template strand, $(rA)_{16}$, was purchased from Dharmacon (Boulder, Co.) as a 1 micromole synthesis, deprotected following manufacture's protocol and purified by passage over a 1 m G-15 size-exclusion column. After passage over the column, sample fractions corresponding to the largest molecular weight products were pooled and freeze-dried. A stock solution of $(rA)_{16}$ was prepared by resuspending the freeze-dried RNA in 1 ml of $dH_2O$. The substrate oligonucleotides 5'-iodo-$(dT)_4$ and ³²P-labeled-3'-phosphorotioate-$(dT)_3$ were prepared as described in Example 1.

Ligation Reactions and Results

Figure 8:
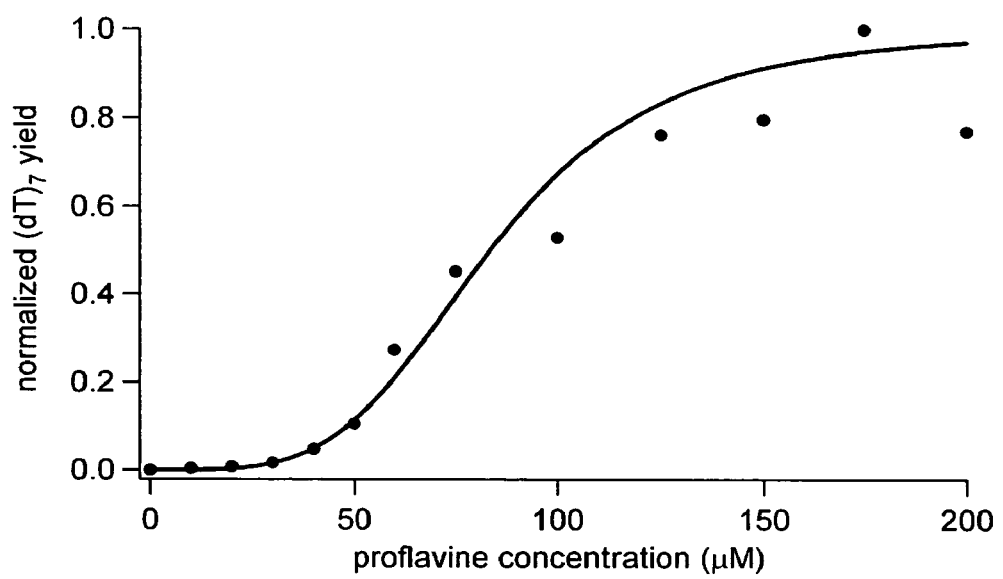
FIG. 8 is a plot of $(dT)_7$ product yield as a function of proflavine concentration for intercalation-mediated ligation experiments using 3'-phosphorothioate-$(dT)_3$ and 5' iodo-$(dT)_4$ as substrates, the RNA template $(rA)_{16}$, and proflavine as the intercalator.
Figure 9:
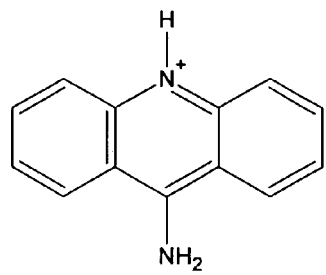
FIG. 9 is a diagram of the molecular structures of representative intercalators.
Figure 9:
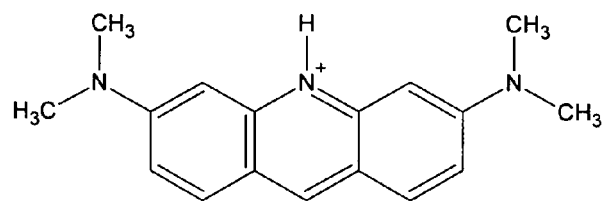
Figure 9:
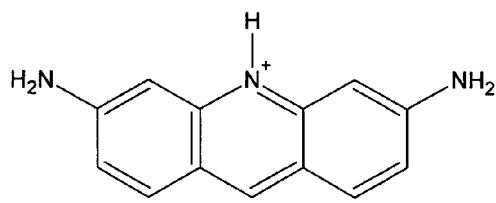
Figure 9:
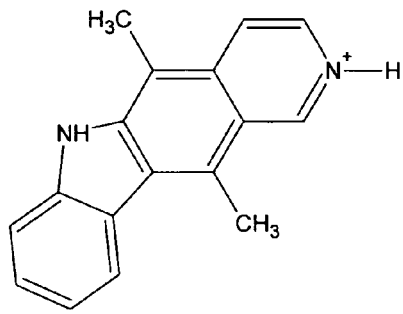
Figure 9:
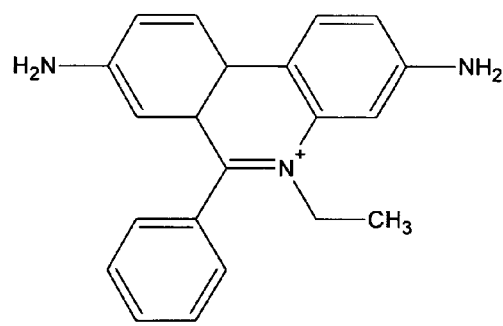
Figure 9:
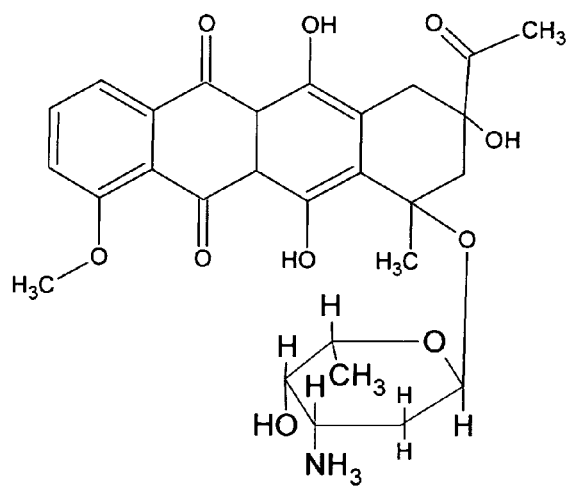

Reactions were carried out in an identical manner as described in Example 1, except that the $(rA)_{16}$ RNA template strand was substituted for the DNA $(dA)_{16}$ template strand. Quantification of product yield was determined by the same method as that described in Example 1. A plot of $(dT)_7$ product yield as a function of proflavine concentration, using an RNA template strand, is shown in FIG. 8.

Example 3

In this example, the present disclosure utilizes the same system described in Examples 1 & 2 except for the use of a different template, which consists of a non-natural oligonucleotide strand, specifically a seven nucleotide strand of 2'-O-methyl-ribo-adenosine (2'-O-methyl-$(rA)_7$).

Synthesis and Purification of Oligonucleotides.

The non-natural RNA template strand, 2'-O-methyl-$(rA)_7$, was prepared using an automated nucleic acid synthesizer and commercial reagents (Beaucage et al., 2000). The substrate oligonucleotides 5'-iodo-$(dT)_4$ and ³²P-labeled-3'-phosphorotioate-$(dT)_3$ were prepared as described in Example 1. The proflavine stock was prepared as described in Example 1.

Ligation Reactions and Results

Figure 10:
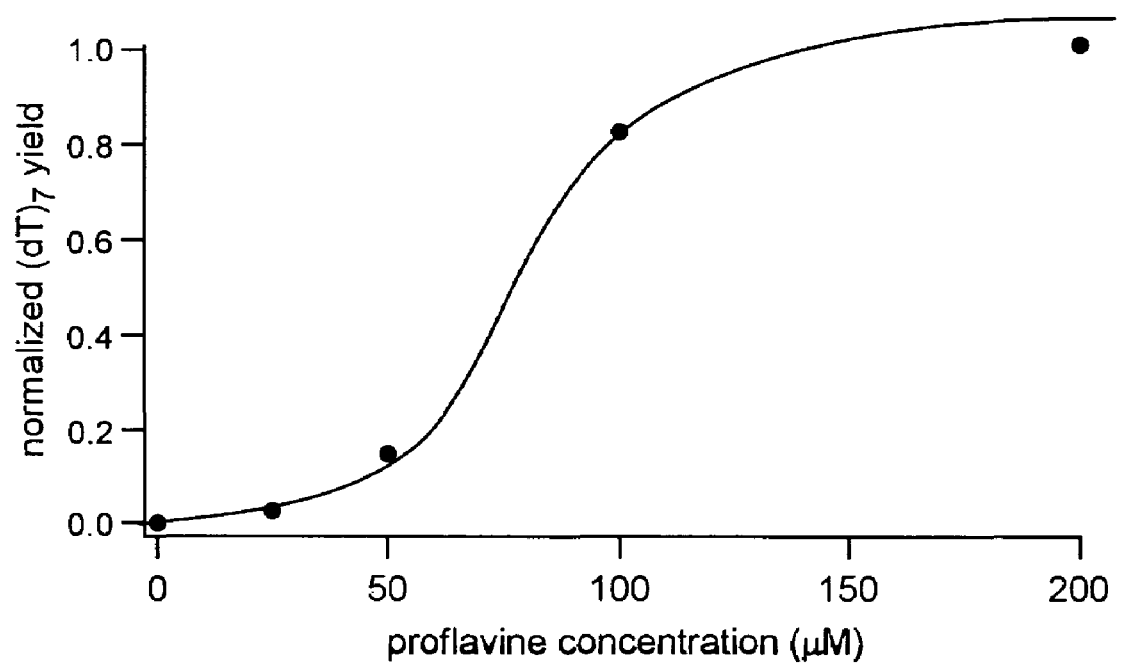
FIG. 10 is a plot of $(dT)_7$ product yield as a function of proflavine concentration for intercalation-mediated ligation experiments using 3'-phosphorothioate-$(dT)_3$ and 5' iodo-$(dT)_4$ as substrates, the non-natural RNA template 2'-O-methyl-$(rA)_7$, and proflavine as the intercalator.

Reactions were carried out in an identical manner as described in Example 2 except that the 2'-O-methyl-$(rA)_7$ RNA template strand was substituted for the RNA $(rA)_{16}$ template. Quantification of product yield was determined by the same method as that described in Example 1. A plot of $(dT)_7$ product yield as a function of proflavine concentration, using the modified RNA template strand, is shown in FIG. 10.

Example 4

Figures 11A, 11B:
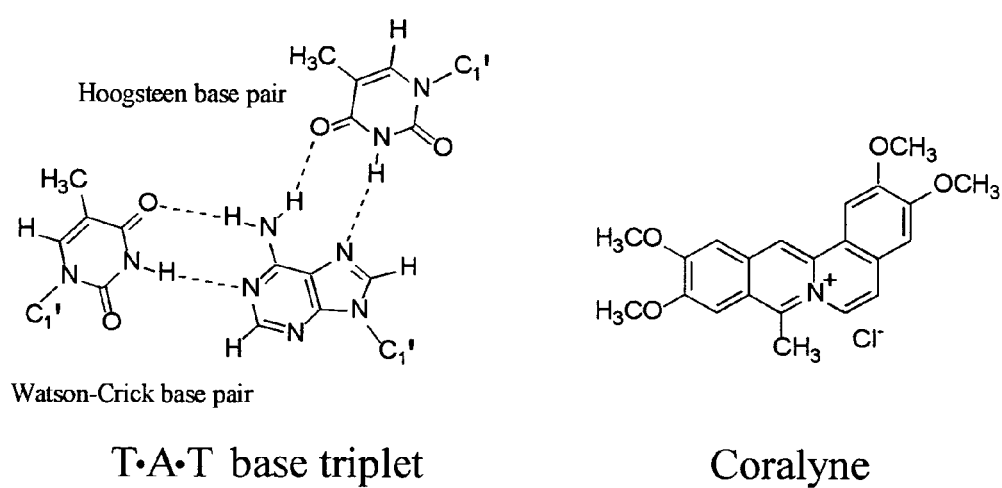
FIG. 11A is the chemical structure of a Watson-Crick A•T•T base triplet.
FIG. 11B is a diagram of the molecular structure of an exemplary intercalator, coralyne.
Figure 12:
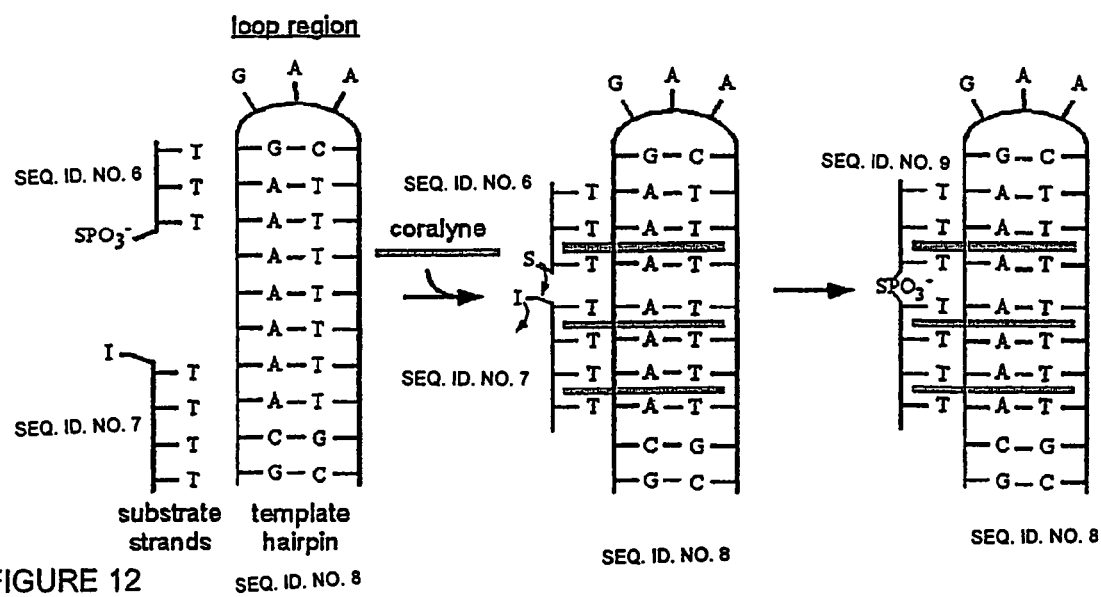
FIG. 12 is a schematic of intercalation-mediated template-directed synthesis showing a duplex template strand in solution with substrate strands and the intercalator, coralyne. The addition of coralyne to the solution facilitated the formation of Hoogsteen base pairs between the purine bases of the template duplex and the pyrimidine bases of the substrate strands.

In this example, the present disclosure as previously described in Examples 1, 2, & 3, can be applied here using a different intercalator, specifically coralyne (FIG. 11). Using coralyne as the intercalator provides for the use of a triplex system instead of the previously described duplex system. Hoogsteen base pairing was used to align the substrates on the duplex template (FIG. 12).

Synthesis and Purification of Oligonucleotides

Synthesis and purification of oligonucleotides were as described in Examples 1, 2, & 3. The particular template, however, was synthesized as a duplex (hairpin-shaped).

Ligation Reactions and Results

Figure 13:
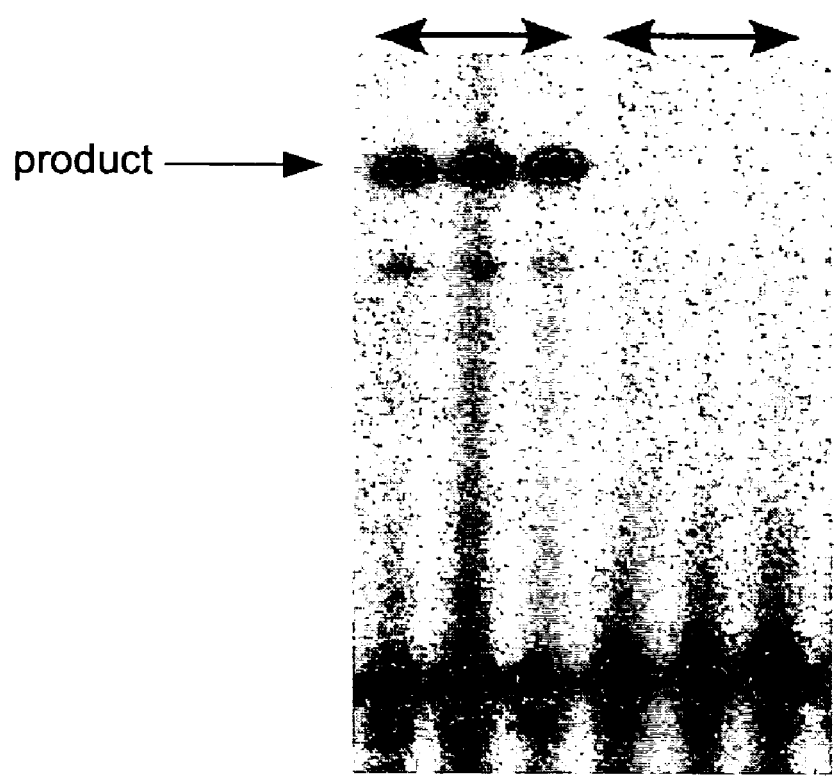
FIG. 13 is an autoradiograph of a polyacrylamide gel run with an intercalation-mediated ligation experiment using 3'-phosphorothioate-$(dT)_3$ and 5'-iodo-$(dT)_4$ as substrates, a duplex template, and the small molecule coralyne as an intercalator. The three left gel lanes show $(dT)_7$ product for the reaction containing coralyne. The three right lanes are for the same reaction without coralyne.

Reactions were carried out in the same manner as described in Example 1 except for the use of coralyn as the intercalator. Gel electrophoresis data for the triplex system using coralyne are shown in FIG. 13.

REFERENCES

The references, including patents on non-patent references, cite here and throughout the disclosure are incorporated by reference in their entirety.

Batiett, J. M. S., and D. Stirling. 2003. *PCR Protocols*. 2nd Ed. ed. Humana Press, Totowa, N.J.

Beaucage, S. L., D. E. Bergstrom, G. D. Glick, and R. A. Jones. 2000. Current Protocols in Nucleic Acid Chemistry. In A. L. Boyle (ed.). John Wiley & Sons, New York.

Brummelkamp, T. R., R. Bernards, R. Agami. 2002. A system for stable expression of short interfering RNAs in mammalian cells. *Science*, 296(5567):550-553.

Ferns, J. P., C. H. Huang, and W. J. Hagan. 1989. N-cyanoimidazole and diimidazole imine—water-soluble condensing agents for the formation of the phosphodiester Bond. *Nucleosides & Nucleotides*, 8:407-414.

Gryaznov, S. M., R. Schultz, S. K. Chaturvedi, and R. L. Letsinger. 1994. Enhancement of selectivity in recognition of nucleic-acids via chemical autoligation. *Nucleic Acids Research*, 22:2366-2369.

Inoue, T., and L. E. Orgel. 1982. Oligomerization of (guanosine 5'-phosphor)-2-methylimidazolide on poly(C). An RNA polymerase model *Journal of Molecular Biology*, 162:201-217.

Kanavarioti, A., C. F. Bernasconi, and E. D. Baird. 1998. Effects of monomer and template concentration on the kinetics of nonezymatic template-directed oligoguanylate synthesis. *Journal of the American Chemical Society*, 120: 8575-8581.

Kanaya, E., and H. Yanagawa. 1986. Template-directed polymerization of oligoadenylates using cyanogen-bromide. *Biochemistry*, 25:7423-7430.

Lin, S. L., and S. Y. Ying. 2001. D-RNAi (Messenger RNA- antisense DNA Interference) as a Novel Defense System Against Cancer and Viral Infections. *Current Cancer Drug Targets*, 1:241-247.

Lohrman, R., and L. E. Orgel. 1978. Preferential formation of (2'-5')-liked internucleotide bonds in non-enzymatic reactions. *Tetrahedron*, 34:853-81.

Lohrmann, R., P. K. Bridson, and L. E. Orgel. 1980. Efficient metal-ion catalyzed template-directed oligonucleotide synthesis. *Journal of the American Chemical Society*, 208:1464-1465.

Pritchard, C. E., and E. M. Southern. 1997. Effects of base mismatches on joining of short oligodeoxynucleotides by DNA ligases. *Nucleic Acids Research*, 25:3403-3407.

Rohatgi, R., D. P. Bartel, and J. W. Szostak. 1996. Kinetic and mechanistic analysis of nonenzymatic, template-directed oligoribonucleotide ligation. *Journal of the American Chemical Society*, 118:3332-3339.

Rubin, E., S. Rumney, S. H. Wang, and E. T. Kool. 1995. Convergent DNA-synthesis—a nonenzymatic dimerization approach to circular oligodeoxynucleotides. *Nucleic Acids Research*, 23:3547-313.

Shabarova, Z. A., N. G. Dolinnaya, V. L. Drutsa, N. P. Melnikova, and A. A. Purmal. 1981. DNA-like duplexes with repetitions 3. Efficient template-guided chemical polymerization of d(TGGCCAAGCTp). *Nucleic Acids Research*, 9:5747-5761.

Shabarova, Z. A., M. G. Ivanovskaya, and M. G. Isaguliants. 1983. DNA-like duplexes with repetitions—efficient template-guided polycondensation of decadeoxyribonucleotide imidazolide. *FEES Letters*, 154:288-292.

Szostak, J, W. 1997. Introduction: Combinatorial chemistry. *Chemical Reviews*, 97:347-348.

von Kiedrowski, G. 1986. A self-replicating hexadeoxynucleotide. *Angewandte Chemie International Edition in English*, 25:932-935.

Xu, Y. Z., and E. T. Kool. 1999. High sequence fidelity in a non-enzymatic DNA autoligation reaction. *Nucleic Acids Research*, 27:875-881.

Zuber, G., and J. F. Behr. 1994. Nonenzymatic plasmid ligation mediated by minor groove-binding molecules. *Biochemistry*, 33:8122-8127.

---

I claim:

1. A method of synthesizing a polynucleotide comprising:
   (a) combining in a fluid:
      (1) a template,
      (2) a plurality of nucleic acid subunits, and
      (3) an intercalator selected from the group consisting of proflavine and coralyne; and
   (b) chemically ligating adjacent nucleic acid subunits associated with the template, wherein the chemical ligation is not medicated by an enzyme.

2. The method of claim 1, wherein the intercalator stabilizes sequence specific associations between nucleic acid subunits and the template.

3. The method of claim 1, wherein the intercalator comprises a planar, polycyclic moiety.

4. The method of claim 1, wherein the intercalator comprises a planar, tricyclic moiety.

5. The method of claim 1, wherein the intercalator comprises proflavine.

6. The method of claim 1, wherein the intercalator facilitates sequence specific interaction between the plurality of nucleic acid subunits and the template.

7. The method of claim 1, wherein at least one of the plurality of nucleic acid subunits is modified to contain a reactive chemical group.

8. The method of claim 1, wherein at least one of the plurality of nucleic acid subunits comprises a methyl-imidazole-activated phosphate.

9. The method of claim 1, wherein the template or at least one of the plurality of nucleic acid subunits comprises RNA, DNA, or a combination thereof.

10. The method of claim 1, wherein the template comprises methylated RNA.

11. The method of claim 1, wherein a chemical bond between the adjacent nucleic acid subunits is formed using a condensing agent.

12. The method of claim 11, wherein the condensing agent comprises 1-(3-dimethylaminopropyl)-3-ethylcarboiimide.

13. The method of claim 1, wherein a chemical bond forms spontaneously between two adjacent nucleic acid subunits.

14. The method of claim 1, wherein at least one of the plurality of nucleic acid subunits comprises two or more linked nucleotides.

15. The method of claim 1, wherein the nucleic acid subunits comprise a modified sugar, modified purine base, modified pyrimidine base, or a combination thereof.

16. The method of claim 1, wherein the synthesized polynucleotide is at least partially complementary to at least a portion of the template.

17. A method of synthesizing a polynucleotide comprising:
(a) combining in a fluid:
(1) a template comprising a methylated RNA,
(2) a plurality of nucleic acid subunits, and
(3) an intercalator comprising proflavine; and
(b) chemically ligating adjacent nucleic acid subunits associated with the template, wherein the chemical ligation is not medicated by an enzyme.

18. The method of claim 17, wherein the intercalator stabilizes sequence specific associations between the nucleic acid subunits and the template.

19. The method of claim 17, wherein the intercalator facilitates sequence specific interaction between the plurality of nucleic acid subunits and the template.

20. The method of claim 17, wherein at least one of the plurality of nucleic acid subunits are modified to contain a reactive chemical group.

21. The method of claim 17, wherein at least one of the plurality of nucleic acid subunits comprises a methyl-imidazole-activated phosphate.

22. The method of claim 17, wherein at least one of the plurality of nucleic acid subunits comprises RNA, DNA, or a combination thereof.

23. The method of claim 17, wherein a chemical bond between the adjacent nucleic acid subunits is formed using a condensing agent.

24. The method of claim 23, wherein the condensing agent comprises 1-(3-dimethylaminopropyl)-3-ethylcarboiimide.

25. The method of claim 17, wherein a chemical bond forms spontaneously between at least two adjacent nucleic acid subunits.

26. The method of claim 17, wherein at least one of the plurality of nucleic acid subunits comprises a modified sugar, purine base or pyrimidine base.

27. The method of claim 17, wherein the intercalator is cationic, anionic, or neutral under conditions that form the chemical bond between the nucleic acid subunits.

28. A method of synthesizing a polynucleotide comprising:
(a) combining a template, an intercalator, and a plurality of nucleic acid subunits in a fluid, wherein the intercalator has a structure according to Formula I:

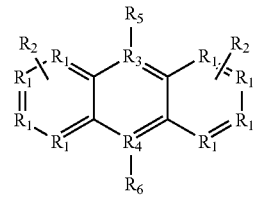

Formula I wherein each $R_1$ and $R_4$ are C;
$R_2$ is independently $NH_2$ or $N(CH_3)_2$;
$R_3$ is N;
$R_5$ and $R_6$ are H; and
(b) chemically ligating the subunits together to form a polynucleotide that is complementary to at least a portion of the template, wherein the chemical ligation is not medicated by an enzyme.

29. The method of claim 28, wherein the intercalator comprises proflavine.

30. The method of claim 28, wherein the intercalator facilitates sequence specific interaction between the plurality of nucleic acid subunits and the template.

31. The method of claim 28, wherein the nucleic acid subunits are modified to contain a reactive chemical group.

32. The method of claim 28, wherein at least one nucleic acid subunit comprises a methyl-imidazole-activated phosphate.

33. The method of claim 28, wherein the template or at least one nucleic acid subunit comprises RNA, DNA, or a combination thereof.

34. The method of claim 28, wherein the template comprises methylated RNA.

35. The method of claim 28, wherein a chemical bond between the nucleic acid subunits is formed using a condensing agent.

36. The method of claim 35, wherein the condensing agent comprises 1-(3-dimethylaminopropyl)-3-ethylcarboiimide.

37. The method of claim 28, wherein a chemical bond forms spontaneously between two adjacent nucleic acid units.

38. The method of claim 28, wherein at least one of the nucleic acid subunits comprises two or more monomers.

39. The method of claim 28, wherein at least one of the plurality of nucleic acid subunits comprises a modified sugar, purine base or pyrimidine base.

40. A method of selecting a polynucleotide comprising:
(a) generating a plurality of polynucleotides having a random sequence of monomers flanked by predetermined sequences of monomers;
(b) selecting a subset of the plurality of the polynucleotides based on binding affinity to a target; and
(c) synthesizing product polynucleotides by intercalator-meditated template-directed synthesis using the subset as templates, wherein the intercalator-meditated template-directed synthesis comprises combining in a fluid the templates, a plurality of nucleic acid subunits, and an intercalator selected from the group consisting of proflavine and coralyne, and chemically ligating adjacent nucleic acid subunits associated with the templates, wherein the chemical ligation is not medicated by an enzyme.

41. The method of claim 40, further comprising the step of sequencing the product polynucleotides.

42. The method of claim 40, further comprising the step of amplifying the product polynucleotides.

43. The method of claim 42, further comprising the step of generating a second plurality of polynucleotides by intercalator-meditated template-directed synthesis using the amplified product polynucleotides as templates.

44. The method of claim 43, further comprising the step of selecting a subset of the second plurality of polynucleotides based on binding affinity to the target.

45. The method of claim 44, further comprising the step of sequencing the subset of the second plurality of polynucleotides.

46. The method of claim 45, further comprising the step of synthesizing a second set of product polynucleotides by intercalator-meditated template-directed synthesis using the selected subset of the second plurality of polynucleotides of claim 45 as templates.

47. The method of claim 46, further comprising the step of sequencing the second set of product polynucleotides synthesized in claim 46.

* * * * *